United States Patent [19]

vanDrongelen et al.

[11] Patent Number: 6,103,814
[45] Date of Patent: Aug. 15, 2000

[54] STYRENIC BLOCK COPOLYMER BASED HOT-MELT ADHESIVES, THEIR USE FOR DISPOSABLE SOFT GOODS, AND TACKIFYING RESINS CONTAINED THEREIN

[75] Inventors: Jan vanDrongelen; Johannes Cornelis M. Simons, both of Grijpskerke, Netherlands

[73] Assignee: Hercules Incorporated, Wilmington, Del.

[21] Appl. No.: 08/843,684

[22] Filed: Apr. 10, 1997

[30] Foreign Application Priority Data

Apr. 15, 1996 [EP] European Pat. Off. .............. 96105882

[51] Int. Cl.$^7$ .................................................. C09J 153/02
[52] U.S. Cl. .......................... 524/505; 524/481; 524/483; 524/484; 524/490; 524/491; 524/499; 524/270; 525/98; 585/365; 585/502; 585/507; 585/525; 585/532
[58] Field of Search ................................ 525/98; 524/481, 524/483, 484, 490, 491, 505, 270, 499; 526/935; 585/365, 502, 507, 525, 532

[56] References Cited

U.S. PATENT DOCUMENTS

| | | | |
|---|---|---|---|
| 5,310,803 | 5/1994 | Hansen | 525/228 |
| 5,378,536 | 1/1995 | Miller et al. | 428/355 |
| 5,389,438 | 2/1995 | Miller et al. | 428/355 |
| 5,443,903 | 8/1995 | Hansen | 428/355 |
| 5,747,573 | 5/1998 | Ryan | 524/270 |

FOREIGN PATENT DOCUMENTS

| | | |
|---|---|---|
| 157293 | 10/1985 | European Pat. Off. . |
| 345124 | 12/1989 | European Pat. Off. . |
| 455105 | 11/1991 | European Pat. Off. . |
| 06234821 | 8/1994 | Japan . |

OTHER PUBLICATIONS

Derwent Abstract of Japanese Patent Application JPA06234821. (1996).

*Primary Examiner*—Mark L. Warzel
*Attorney, Agent, or Firm*—Robert P. O'Flynn O'Brien

[57] ABSTRACT

Disclosed are hot-melt adhesive compositions suitable for the manufacture of soft goods. They have a melt viscosity of 60,000 mPa.s or less at a temperature of 120° C. and include: (a) 50 to 150 parts by weight of a styrenic block copolymer or mixtures and/or modified and/or hydrogenated derivatives thereof; (b) 20 to 450 parts by weight of a tackifying resin which, when incorporated into a reference composition, leads to the following properties:

a tan $\delta$ value of 3.5 or less, wherein tan $\delta$ is defined as the ratio between the loss modulus and the storage modulus of said composition and an elastic retention on spandex fibers (300%) or natural latex rubber (200%) after 4 h at 40° C. of 70% or more; and a crossover temperature of 95° C. or less.

Further disclosed are novel partially hydrogenated hydrocarbon resins which are useful as tackifying resins and have the following properties: (a) a R&B softening point (R&B) of 50° C. to 150° C.; (b) a mixed methylcyclohexane aniline cloudpoint (MMAP) of 10° C. to 75° C.; (c) a Di-Acetone Alcohol cloudpoint (DACP) of 35° C. or less; (d) a molecular weight (Mz) of 10,000 Dalton or less; and (e) a UV absorbance at 268 nm ranging from 2.0 to 5.0.

33 Claims, No Drawings

STYRENIC BLOCK COPOLYMER BASED HOT-MELT ADHESIVES, THEIR USE FOR DISPOSABLE SOFT GOODS, AND TACKIFYING RESINS CONTAINED THEREIN

FIELD OF THE INVENTION

This invention relates to thermoplastic compositions designed as adhesives, particularly as multi-purpose hot-melt adhesives. In particular, this invention relates to sprayable hot-melt adhesive compositions which may be used to bond or construct articles in the manufacture of disposable soft goods such as diapers, feminine napkins and the like.

BACKGROUND OF THE INVENTION

Hot-melt adhesives are thermoplastic compositions which are solid at room temperature. When heated to a liquid or molten form, the hot-melt adhesive can be applied to a substrate. If a second substrate is placed on the hot-melt adhesive before it cools back to a solid, an adhesive bond can be formed joining the two substrates.

Especially hot-melt compositions based on styrenic block copolymers, tackifying resins, and plasticizing oils, have been employed in a wide variety of product assembly applications, mainly in the diaper or feminine napkins production for the manufacture of disposable soft goods. A particularly preferred application is their use in bonding lightweight materials such as, but not limited to, polyethylene or polypropylene substrates to paper, fabric, tissue, non-wovens, polyethylene or polypropylene substrates or to themselves. Specific applications for such prior art adhesives have included sanitary napkins, disposable diapers, surgical drapes, adult incontinent products, hospital pads and other products like these.

Multi-purpose adhesive compositions are those adhesives which can be used for more than one application. It should be understood that, for example, in the manufacture of most disposable diapers, today, several different adhesive applications are present. These adhesive applications include:

1) the use of adhesives in construction, that is, bonding the polyethylene to the nonwoven and absorbent pad;
2) the use of adhesives for landing strips, that is, bonding a reinforcing layer of a polyolefin film to the polyethylene in the area opposite the tape tabs;
3) the use of adhesives for elastic attachment, that is, bonding the elastic material to the polyethylene in either the leg and/or waist area; and
4) the use of core adhesives, that is, applying an adhesive to the absorbent core to increase the strength of the core.
5) for bonding a non-woven material to the backsheet of a diaper and,
6) as a multi-purpose adhesive.

The methods of application of these prior art adhesives have included, but are not limited to, spray or wheel application systems or (multi-bead or slot) extrusion. One of the most critical parameters during the application of the hot-melt adhesive is the "open-time" of the adhesive. "Open-time" is the time during which the adhesive is applied to a first substrate and remains sufficiently molten to effect a bond between the first substrate and a second substrate.

Once the open-time has been exceeded, the second substrate cannot be readily bonded to the first substrate, unless the adhesive exhibits a high degree of tack or pressure sensitivity, which, however, manifests itself in poor cohesive strength. Since sufficient cohesive strength of the adhesive is one of the key properties, such adhesives cannot be formulated as multi-purpose adhesive compositions. The adhesive must possess sufficient cohesive strength to provide high bond strength values when subjected to stress, either at ambient or elevated temperatures, so that the bonded parts cannot be easily separated. For example, it is very important that a construction adhesive for disposable soft goods maintains its bond not only at room temperature but also at elevated temperatures, that is 38° C. (100° F.). This elevated temperature resistance is important because without this characteristic, delamination of the end product occurs if the adhesive bond comes into contact with the user's skin. Apart from a high level of cohesion, long open-times are generally preferred for multi-purpose adhesives, because the wettability of the system towards the substrate is thereby improved, that is, the molten adhesive is allowed a longer period to spread out onto the substrate, which will improve its adhesion to the substrate.

As an additional criteria, it is necessary that the adhesive, upon application, is not absorbed into the actual disposable construction, and that the adhesive bonds not only remain secure, but also flexible even after prolonged periods of storage. In addition to requiring heat and oxidation resistance on aging, they should also possess a sufficient bonding range and must be light or clear in color. Moreover, since the adhesive is applied at high temperatures, excellent odour characteristics are required and it is of vital importance that the final compound does not irritate or sensitize the human skin to any extent.

Recently, many disposable garment manufacturers have begun to use spray application techniques. Spray application generally permits contact and ready application to uneven and irregular surfaces. Because spray application also allows for coating of less than the entire surface, spray application can reduce the amount of material used. Spray application is particularly useful where air or moisture permeability is desired. In addition there may be less risk of thermal damage to substrates than with other application methods.

Changes in diaper manufacturing have brought about the development of new hot-melt adhesives. Diaper manufacturers now use thinner gauge polyethylene to manufacture diapers. Not only does thinner gauge polyethylene produce a more aesthetically pleasant diaper but it also represents significant cost savings. However, as the gauge of the polyethylene is decreased, the likelihood of a burn through of these thin layers increases. In the past, the lower limit on the operating temperature was defined by the temperature at which the hot-melt adhesive could be applied with sufficiently low viscosity for even and proper application. Such temperatures were generally in the range of 150° C. to 180° C. It would be beneficial if hot-melt adhesives could be applied at temperatures of from about 120° C. to about 150° C.

It is therefore one of the objects of the present invention to provide a hot-melt adhesive composition which can be sprayed at such low temperatures.

Styrenic block copolymers are widely used to make hot-melt adhesives for a variety of uses, including diaper assembly. These styrenic block copolymers include unvulcanized elastomeric block copolymers wherein the respective monomeric moieties are arranged in an alternating sequence having the general configuration A-B-A.

In this configuration, A is a non-elastomeric block derived from styrene, usually referred to as styrenic "end-block", and B is an elastomeric polymer block derived from, for example, isoprene and/or butadiene, usually indicated as, for example, isoprene or butadiene "mid-block". This type of block copolymer may also be described as having a branched polymerized mid-block, derived from, for example, isoprene or butadiene, with a polystyrene terminal block at the end of each branch.

At temperatures of about 175° C. or higher, adhesive systems based on styrenic block copolymers usually act as a homogeneous melt. The system is in the so-called "disordered" state. With decreasing temperatures, however, the polymer end-blocks, although connected to the elastomeric mid-blocks, have a strong preference to segregate from the mid-block phase, because of their inherent thermodynamic incompatibility. The mid-blocks and end-blocks are only compatible with each other at very high temperatures, such as, for example 175° C. Because of this, the polymer mid-blocks and end-blocks start to segregate in two discrete phases during the cooling cycle of the adhesive, thereby inducing, a gradual, but significant increase in viscosity, plateau modulus, and cohesion of the adhesive, which appears to be more significant compared with systems which remain homogeneous during the cooling cycle.

It should be understood, however, that the mid-blocks and end-blocks of styrenic block copolymers remain connected to each other over the whole temperature range.

The segregation of the end-blocks is therefore better described by the phenomenon that the glassy polystyrene end-blocks start to associate into discrete "hard" domain structures, generally referred to as end-block domains.

This agglomeration process occurs because of their inherent thermodynamic incompatibility with the mid-block phase. These end-block domain structures act like a physical crosslink, thereby reducing the mobility of the adhesive, that is, they increase the viscosity, plateau modulus, and cohesive strength of the system. This process is temperature-reversible, that is, the domain structures will gradually disappear again when the temperature is increased. The glassy styrenic domains will soften and flow under heat and shear, temporarily disrupting the physical crosslink and allowing thermoplastic compounding and fabrication; upon cooling, the domains reform and the elastomeric character is restored. The domain formation process is usually called the "order-disorder transition" of the styrenic block copolymer. It starts at a specific temperature, that is, the temperature at which the first signs of incompatibility between the polymer mid-blocks and end-blocks become manifest.

The order-disorder transition of the system is accomplished gradually during the cooling cycle of the system and ends when all styrenic end-blocks have agglomerated into domains, that is, are grouped in an ordered state throughout the adhesive. Adhesives with a higher percentage of styrene as a total of the entire compound, usually exhibit a higher order-disorder transition temperature.

In some cases, certain tackifying resins are able to delay the order-disorder transition process, especially those containing a certain amount of polar or aromatic components, such as, for example, rosin esters, aromatically modified aliphatic resins or partially hydrogenated aromatic resins.

Tackifying resins which delay the order-disorder transition process, appear to postpone the significant increase in cohesion and viscosity caused by the mid-block and end-block phase segregation. It is believed that a larger amount of the styrenic end-blocks remains mobile in the system, or is presumably still partially compatible with the mid-block phase. This is highly beneficial for increasing the open-time of adhesives based on such styrenic block copolymers. For systems containing resins with only a limited amount of polar or aromatic components, the order-disorder transition process is usually completed at temperatures below approximately 45° C.–50° C. In this case, it is believed that the styrene end-blocks, which are incompatible with the mid-block phase at these temperatures, have all agglomerated into segregated rigid domains, acting like physical crosslinks which connect the polymer mid-blocks, thereby enhancing the cohesive strength and increasing the plateau modulus of the system.

It should be recognized that a higher percentage of styrenic end-block domains in the system will enhance the cohesive strength of the adhesive, will raise its plateau modulus and will improve its elevated temperature resistance.

However, it became evident following experimentation that the incorporation of tackifying resins and/or plasticizing oils containing a significant amount of polar or aromatic components into styrenic block copolymer based hot-melt adhesives often resulted in a significantly reduced cohesive strength and elevated temperature resistance of the adhesive. This effect appeared for all types of styrenic block copolymers, such as, for example, S-B-S (styrene-butadiene-styrene); (S-B)n (styrene-butadiene-styrene); S-I-S (styrene-isoprene-styrene); S-V-S (styrene-vinylbutadiene-styrene); S-EB-S (styrene-ethylene/butylene-styrene); and S-EP-S (styrene-ethylene/propylene-styrene) copolymers.

Although systems formulated with tackifying resins containing a significant amount of polar or aromatic components were found to have adequate adhesion properties in some cases, they showed a disadvantage because of their poor elevated temperature creep resistance and relatively low level of cohesive strength. As a result of the foregoing it was believed that adhesive compositions based upon styrenic block copolymers in combination with such tackifying resins would not be well suited for use as multi-purpose adhesives.

It is therefore another object of the of the present invention to identify a resin useful as a tackifying resin in styrenic block copolymer based hot-melt adhesive compositions, which resin maintains or improves the adhesion, wettability and open-time of the system without significantly reducing the cohesive strength and elevated temperature resistance of the adhesive.

Hot-melt adhesives based on styrenic block copolymers such as, for example, "Kraton®" thermoplastic rubber are said to provide excellent adhesion to non-polar substrates, such as polyethylene, which are commonly used in diaper manufacture. Additionally, these adhesives are said to maintain adhesion in elasticity demanding applications such as disposable diapers. Relatively low styrene content (from 15% to 24%) styrene-isoprene-styrene (S-I-S) block copolymers are said to be useful in adhesives for such applications.

In addition to the adhesives discussed above, adhesives based on styrene-butadiene-styrene block copolymers, such as S-B-S or (S-B)n copolymers, have been suggested for use in the construction of disposable soft. goods. Relatively high styrene content (from 25% to 50%) styrene-butadiene-styrene block copolymers are said to be useful in adhesives for such applications. Styrene-butadiene-styrene block copolymers, in particular S-B-S or (S-B)n block copolymers, or mixtures thereof, are hereafter abbreviated with the general designation S-B-S block copolymers.

The use of S-B-S block copolymers has proved particularly troublesome to the adhesive industry in terms of identifying a suitable tackifying resin. It has been known in preparing adhesives using S-I-S block copolymers that aliphatic tackifying resins may be used with success.

Unfortunately, the aliphatic resins, while meeting the requirements for lower color adhesives, do not have adequate compatibility with S-B-S copolymers to form an acceptable adhesive.

It has been found that the desired adhesive properties are not present with aliphatic tackifying resins in S-B-S systems because of the higher mid-block solubility parameter component of S-B-S copolymers versus S-I-S copolymers. While aliphatic tackifying resins, with relatively low solubility parameters, are compatible with the mid-block of S-I-S block copolymers, they exhibit limited compatibility with the mid-block of S-B-S copolymers having a higher solubility parameter. The problem is even made worse by the use of oil in many formulations. If a more aromatic tackifying resin is used, a more compatible blend is formed with the S-B-S mid-block, particularly in the presence of oils. In order to maintain sufficient wettability to polyolefinic substrates adhesive compositions employing commercially available S-B-S copolymers were formulated with tackifying resins which exhibited a low to medium degree of functionality, such as partially hydrogenated aromatic resins, aromatically modified aliphatic C-5 resins or aromatically modified polyterpene resins, thus resins which showed adequate butadiene mid-block compatibility. These S-B-S based adhesive compositions appeared to be improvements over the previously employed adhesives in several important respects, but they also had several drawbacks which detracted from their usefulness.

For example, it was discovered that when an S-B-S based adhesive composition was left in an adhesive applicator for an extended period of time, it would rapidly increase in viscosity and ultimately gel thereby making its removal extremely difficult. Furthermore, adhesive compositions based upon S-B-S copolymers often showed poor adhesion properties, and did not appear to have sufficient elevated temperature creep resistance to perform well as an elastic attachment adhesive, or to bond a roamed elastic waistband to the disposable diaper, as compared with adhesive compositions based upon styrene- isoprene-styrene (S-I-S) block copolymers. Those skilled in the art will recognize that it is more difficult to tackify S-B-S copolymers than S-I-S copolymers. In this regard S-B-S systems are believed to possess a lower degree of adhesion, when compared with S-I-S adhesives.

In view of the prior art difficulties with formulating an appropriate multi-purpose S-B-S adhesive, one might think that adhesive compositions based upon S-B-S copolymers formulated with highly polar resins like, for example, rosin esters, could be suitable for that use. Rosin is a solid material that occurs naturally in the oleo resin of pine trees and typically is derived from the oleo resinous exudate of the living tree, from aged stumps and from tall oil produced as a by-product of kraft paper manufacture. After it is obtained rosin can be treated by hydrogenation, dehydrogenation, polymerization, esterification, and other post treatment processes. Rosin is typically classed as a gum rosin, a wood rosin, or as a tall oil rosin depending on its source. The material can be used unmodified, in the form of esters of polyhydric alcohols, or can be polymerized through the inherent unsaturation of the molecules. These highly polar materials are commercially available and can be blended into adhesives using standard blending techniques.

Representative examples of such prior art rosin derivatives, include pentaerythritol esters of tall oil rosin, gum rosin, wood rosin, or mixtures thereof. Adhesive compositions containing such highly polar rosin esters appeared to be improvements over the previously employed adhesives in several important respects, but they also had several drawbacks, which detracted from their usefulness. For example, it became evident following experimentation that resins which contain a significant amount of polar or aromatic components tended to show a weaker cohesive strength and less elevated temperature resistance. As a result, it was believed that adhesive compositions containing prior art rosin esters would not be ideally suitable for use as multi-purpose adhesives.

It is therefore another object of the present invention to identify a suitable tackifying resin and provide a hot-melt adhesive composition containing same, wherein even in an S-B-S based system the adhesion, wettability and open time are maintained or improved without significantly reducing the cohesive strength.

As discussed earlier, long open-times are preferred when the molten adhesive is applied to the substrate. Especially for application techniques such as spray application of the adhesive, longer adhesive open-times are very important. When the molten adhesive is sprayed, it will be understood that immediately after the adhesive composition is extruded through a nozzle, it is picked up by an air stream which transports the adhesive composition to the desired substrate.

This method of applying an adhesive tends to reduce the temperature of the adhesive composition, when compared to other application systems, even if the air stream is heated. This fast cooling effect usually induces a substantial decrease in the wettability and open-time of the hot melt adhesive. As a result of this, this particular method of application is more critical with respect to the viscosities and open-times.

Additionally the adhesive composition is substantially elongated by this process, which further enhances the cooling effect because the adhesive composition increases in its overall surface area. Because of this cooling effect, the open-time of the adhesive is markedly decreased, whereby the wettability of the adhesive, and consequently its adhesion to the substrate, is significantly reduced.

It is therefore an object of the present invention to provide a hot-melt adhesive composition having a longer open-time than previously known adhesives based on predominantly aliphatic resins, particularly when applied by a spray application technique.

In an attempt to improve the cohesion at body temperature of S-I-S based compositions, end-block reinforcing resins, such as, for example Endex® 155 Hydrocarbon Resin, were blended with same. However, these resins appeared to decrease the specific adhesion of the adhesive compositions to polyolefin substrates and also raised the raw material cost of the final adhesive composition inasmuch as these reinforcing resins are generally quite expensive.

Prior art adhesives containing end-block reinforcing resins also have had the noteworthy deficiency of an undesirable high viscosity and a reduced wettability and open-time of the system, making these systems unsuitable for spraying applications. This is shown below in Examples 22 through 25.

It is therefore another object of the present invention to provide tackifying resins and end-block compatible resins offering improved adhesion properties and open-times in styrenic block copolymer based hot-melt adhesive systems, and additionally providing enhanced cohesive strength at room and body temperature.

In addition to the adhesives discussed above, it has been suggested that adhesive compositions based upon high styrene S-I-S copolymers formulated with stryrenated polyterpene resins and/or highly polar resins like rosin esters, could be suitable for use as multi-purpose adhesives. Especially preferred were pentaerythritol esters of tall-oil rosin, wood rosin or gum rosin, or mixtures thereof. Relatively high styrene content (from 25% to 50%) styrene-isoprene-styrene block copolymers are said to be useful in adhesives for such applications. Such adhesive compositions appeared to be improvements over the previously employed adhesives in several important respects, but they also had several drawbacks, which detracted from their usefulness.

Namely, it became evident following experimentation that resins containing a significant amount of polar or aromatic components tended to decrease the elevated temperature resistance of the final compound significantly. In addition to this, these resins allowed to obtain only a reduced cohesive strength of the continuous phase of the adhesive wherein said continuous, phase comprises the polymer midblocks, the tackifying resin and the plasticizing oil. Thus, although these systems may possess adequate adhesion properties, they usually displayed a relatively poor elevated temperature resistance and a relatively low cohesive strength.

Furthermore, hot-melt adhesives based on highly polar resins, especially those based on the conventional rosin esters, tend to have poor odour characteristics in comparison with systems based on hydrogenated resins. Moreover, it has been speculated that some systems based. on conventional rosin esters may sensitize the human skin to some extent. It should be understood that systems based on rosin esters exhibit long open-times and excellent adhesion to polyolefinic substrates, but that the above mentioned drawbacks, which detracted from their usefulness, have urged the adhesive industry to seek for resins which can replace the conventional rosin esters in their adhesive formulations.

The present invention replaces the conventionally used rosin esters and styrenated polyterpene resins in styrenic block copolymer adhesive compositions, such as, for example, S-I-S formulations, by tackifying resins, which offer comparable adhesion properties and open-timers in S-I-S systems, and additionally provide enhanced cohesive strength at room and body temperature. In addition, these hot-melt adhesive compositions should exhibit excellent odour characteristics and should not irritate or sensitize the human skin to any extent.

Also, the present invention provides improved hot-melt adhesive compositions which are uniquely suited for the manufacture of disposable soft goods, particularly as a multi-purpose hot-melt adhesives for disposable diapers, feminine napkins and the like. They should further be particularly suitable for a spray application technique, even under lower temperatures.

Additionally, the present invention provides hot-melt construction adhesives, based on styrenic block copolymers or mixtures thereof, which have a high degree of specific adhesion without simultaneously suffering from a loss of cohesive strength, either at ambient temperatures or elevated temperatures. Additionally, the adhesives should possess a sufficient elevated temperature resistance, good wettability, long open-times and no tendency to increase in viscosity or gel even under prolonged heat aging at application temperatures.

Additionally, present invention provides hot-melt adhesives which are formulated in either single or multi-purpose adhesive products without the need of employing the reinforcing resins which were previously considered essential. The adhesives should form strong bonds to polyolefin substrates, elastic materials, that is, natural rubber latex, Lycra® or polyethylene elastic, and tissue and nonwoven substrates. Furthermore, they should have an improved creep resistance as compared to the prior art styrenic block copolymer based adhesives employed heretofore.

Hot-melt adhesives of the present invention are of utility for the purposes described above and which are durable, easy to apply utilizing conventional manufacturing techniques, and which further do not have the numerous shortcomings attributable to the prior art construction adhesives used heretofore.

Tackifying resins of the present invention impart a high degree of specific adhesion to styrenic block copolymer based hot-melt adhesives, and additionally provide longer open-times and enhanced cohesive strength both at ambient temperatures and elevated temperatures. The tackifying resin should impart these positive properties to any styrenic block copolymer based hot-melt adhesive composition, particularly to sytems based on S-I-S, S-B-S, S-V-S and (S-B)n block copolymers.

SUMMARY OF THE INVENTION

The above objects are attained by a hot-melt adhesive composition which comprises:

(a) about 50 to about 150 parts by weight of a styrenic block copolymer or mixtures and/or modified and/or hydrogenated derivatives thereof;

(b) about 20 to about 450 parts by weight of a tackifying resin which, when incorporated into a reference composition consisting of 100 parts by weight of a styrene-isoprene-styrene copolymer having a styrene content of 20–30% by weight, 250 parts by weight of said tackifying resin, 50 parts by weight of a paraffinic/naphthenic (70/30) extender oil and 2 parts by weight of a stabilizer consisting essentially of pentaerythrityl-tetrakis[3-(3,5-di-tert.butyl-4-hydroxyphenyl)-propionate], leads to the following properties of said reference composition:

a melt viscosity of about 60,000 mPa.s or less at a temperature of 120° C.;

a tan δ value of about 3.5 or less, wherein tan δ is defined as the ratio between the loss modulus and the storage modulus of said composition;

an elastic retention on spandex fibers (300%) or natural latex rubber (200%) after 4 h at 40° C. of about 70% or more; and a crossover temperature of about 95° C. or less.

Spandex fibers comprise segmented polyurethane comprising linear block copolymers (Lycra® fibers available from E.I. du Pont de Nemours & Company, Incorporated).

In a preferred embodiment, the hot-melt adhesive compositions of the present invention contain a tackifying resin which is a partially hydrogenated hydrocarbon resin having the following properties:

(a) a Ring and Ball softening point (R&B) of about 50° C. to about 150° C.;

(b) a mixed methylcyclohexane aniline cloudpoint (MMAP) of about 10° C. to about 75° C.;

(c) a Di-Acetone Alcohol cloudpoint (DACP) of about 35° C. or less;

(d) a z-average molecular weight (Mz) of about 10,000 Dalton or less; and (e) a UV absorbance at 268 nm ranging from about 2.0 to about 5.0.

Most preferably, this tackifying resin is a partially hydrogenated aromatic C9 hydrocarbon resin.

In a further preferred embodiment, the hot-melt adhesive compositions of the present invention further contain a vicosity modifying aromatic resin having the following properties:

an R&B softening point of about 50° C. to about 150° C.;

an MMAP cloudpoint of about 20° C. or less a DACP cloudpoint of about 0° C. or less, and an Mz value of about 15,000 Dalton or less.

The above numerical ranges indicated for parts by weight of the respective components and for other parameters may in some cases be exceeded to a limited extent (generally about ±10%, in some cases even ±20% or more) without failing to attain the overall effects of the present invention. The invention should be construed to cover such deviations.

In one embodiment, the invention comprises a process of assembling a product utilizing the hot-melt adhesive composition. The process comprising the steps of, providing a first substrate, heating a hot-melt adhesive composition to a liquid or molten form. The hot-melt adhesive is applied in liquid or molten form to the first substrate. A second substrate is provided and placed in contact with the hot-melt adhesive in liquid or molten form applied to the first substrate, forming an adhesive bond between the first substrate and the second substrate. The hot-melt adhesive composition may be sprayed onto the first substrate. The products so assembled may comprise a disposable diaper or a feminine napkin.

DETAILED DESCRIPTION OF THE INVENTION

In the following description and examples, all parts and percentages are given by weight unless otherwise indicated.

The hot-melt adhesives of the present invention are now described in detail by reference to their composition and their properties.

Quite generally, the hot-melt adhesive compositions of the present invention comprise:

(a) a styrenic block copolymer component, (b) a tackifying resin, (c) optionally, a plasticizing oil, (d) optionally, a stabilizer and (e) optionally, a viscosity modifying resin.

The amounts (in parts by weight) of the individual components in the hot-melt adhesive compositions of the present invention are:

(a): about 50 to about 150, preferably about 70 to 125, most preferably approximately 100;

(b): about 20 to about 450, preferably about 150 to 300, most preferably approximately 250;

(c): about 150 or less, e.g. about 5 to about 150, preferably about 30 to about 100, most preferably approximately 50;

(d): about 4 or less, e.g. about 0.1 to about 4, preferably about 0.5 to 3, most preferably approximately 2;

(e): about 100 or less, preferably about 50 or less, most preferably approximately 25.

Styrenic Block Copolymer Component (a)

The Styrenic Block Copolymer Component used in the hot-melt adhesive compositions of the present invention is any styrene containing block copolymer or mixture thereof, including modified and/or hydrogenated derivatives thereof. Examples are S-I-S, S-B-S, S-V-S or (S-B)n block copolymers, or mixtures thereof, including modified and/or hydrogenated derivatives thereof, wherein S is styrene, I is isoprene, B is butadiene, and V is vinyl isoprene or vinyl butadiene. The styrene content is preferably between about 10% to about 80% of the total weight of the block copolymer. The end-blocks of the copolymer are composed of styrene derived (=styrenic) moieties. The most preferred styrenic block copolymer is an S-I-S block copolymer and an S-B-S block copolymer. However, the present invention is not limited to these types of styrenic copolymers.

S-I-S Block Copolymers

A preferred multi-purpose adhesive composition of the present invention contains about 100 parts of an S-I-S block copolymer, including modified and/or hydrogenated derivatives thereof, containing 20 to 28% and preferably 25% styrene (by weight of the entire block copolymer), about 250 parts of a compatible tackifying resin; about 50 parts by weight of a naphthenic/paraffinic mineral oil; and 0.5 to 4.0 parts by weight of a suitable antioxidant:.

The S-I-S block copolymer component of the hot-melt adhesives of the present invention may be one of two specific classes:

(a') An unvulcanized elastomeric block copolymer wherein the respective monomeric moieties are arranged in an alternating sequence having the general configuration A-B-A-B-A-B- or A-B-A.

(a") A teleblock copolymer comprising molecules having at least three branches radially branching out from a central hub, each of said branches having polystyrene terminal blocks and an isoprene segment in the center.

These two classes are further described below:

In class (a'), A is preferably a non-elastomeric block derived from styrene and B is preferably an elastomeric polymer block derived from isoprene or vinyl isoprene.

The non-elastomeric blocks, referred to in both specific copolymer classes (a') and (a"), which preferably make up 10% to 80% by weight of the block copolymer may comprise homopolymers or copolymers of vinyl monomers such as vinyl arenes, vinyl pyridines, vinyl halides and vinyl carboxylates, as well as acrylic monomers, such as acrylonitrile, methacrylonitrile, esters of acrylic acids, etc. Monovinyl aromatic hydrocarbons include particularly those of the benzene series, such as, styrene, vinyl toluene, (alpha)methyl-styrene, vinyl xylene, ethyl vinyl benzene as well as dicyclic monovinyl compounds, such as, vinyl naphthalene and the like. Other non-elastomeric polymer blocks may be derived from alpha olefins, alkylene oxides, acetals, urethanes etc. Styrene is usually preferred as non elastomeric block.

The elastomeric block component, referred to in both specific copolymer classes (a') and (a"), which makes up the remainder of the copolymer, is preferably isoprene or vinyl isoprene, which may or may not be modified or hydrogenated, either partially or substantially complete. Selected conditions may be employed, for example, to hydrogenate the elastomeric isoprene block, while not so modifying the vinyl arene polymer blocks.

Other conditions may be chosen to hydrogenate substantially uniformly along the polymer chain, both the elastomeric and non-elastomeric blocks thereof being hydrogenated to practically the same extent, which may be either partial or substantially complete.

In the present invention, the total concentration of styrene in the block copolymer may range from e.g. about 10% to about 80% of the total weight of the copolymer. A more preferred range is 20% to 60%. Suitable styrene-isoprene-styrene block copolymers for use herein are commercially available from Enichem Americas under the trade-name "Europrene® Sol T".

The preferred block copolymer for use in the compositions of the present invention is "Europrene® Sol T 193B". Other commercially available polymers include, for example, those polymers manufactured under the trademarks "Europrene® Sol TE 9407", "Kraton® D-KX 602CS", "Kraton® D-1125", "Vector® 4211" and "Vector® 4411". "Kraton®" polymers are manufactured by Shell Chemical Company and "Vector®" polymers are produced by The Dexco Chemical Company. All of these commercial polymers are further characterized in the Materials & Methods section below.

The teleblock copolymer of class (a") may also be described as having a branched polymerized isoprene midblock with a polystyrene terminal block at the end of each branch. Radial block copolymers contain about 10 to 60 percent, most preferably 25 to 35 percent of interpolymerized units derived from styrene. The number average molecular weight (determined by GPC) of the preferred radial block copolymers is in the range of about 50,000 to 500,000, more preferably from about 90,000 to about 350,000 and most preferably greater than about 160,000. Particularly preferred radial block copolymers are isoprene and styrene-based copolymers wherein the polystyrene block molecular weight is greater than 12,000 and the polystyrene content is 35 percent or less based on the total weight of the copolymer.

Mixtures of the above block copolymers, including modified and/or hydrogenated derivatives thereof, may also be used as base copolymer components in the adhesives employed for use in manufacturing disposable soft goods. It should be understood, however, that adjustment of the range of styrene, that is, the weight percentage of styrene as compared with the total weight of the S-I-S copolymer, below 20% or above 28% as specified herein, may produce less favorable results in the above suggested preferred formulation though it still is within the scope of the present invention. Adjustment of the percentage of tackifying resin or plasticizing oil may in that case be advantageous to obtain an improved performance.

As will be shown hereinafter, the inventors of the present invention have discovered particularly surprising advantages when they employed S-I-S copolymers which have, as a percentage of the total weight of the copolymers, a styrene content in the range of about 20% or higher.

In particular, it was discovered that the hot-melt adhesive compositions according to the present invention which are formulated with particular tackifying resins as described below display an unusually desirable adhesive performance with block copolymers having higher styrene contents, in comparison with prior art compositions based on commercially available non-functional aliphatic C5 resins, partially or totally hydrogenated resins, aromatically modified aliphatic resins, styrenated polyterpene resins, and even rosin esters. This advantage is obtained without a simultaneous loss of cohesive strength, either at ambient temperatures or elevated temperatures. This is shown by reference to Examples 1 through 8.

These comparative test results will be discussed in greater detail hereinafter. To better appreciate the surprising results achieved by the present invention, it should be understood that, heretofore, such prior art styrenic block copolymer compounds were not considered particularly useful in hot-melt adhesive compositions for soft goods because they exhibited an unusually high viscosity and/or a low cohesive strength, either at ambient temperatures or elevated temperatures. Therefore, in an attempt to employ these same substances in manufacturing adhesive compositions, those skilled in the art utilized di-block substances, such as, for example, S-I (styrene-isoprene) or S-B (styrene-butadiene) di-blocks, especially in, but not limited to, S-I-S or S-B-S compositions, to reduce the viscosity to acceptable levels.

Though the composition of the present invention may also contain up to about 30% of di-block substances, such as, for example S-I or S-B di-blocks, such di-blocks are not essential to obtain the effect of the present invention and a high tri-block content copolymer is preferred. Di-blocks may be present as an impurity in the manufacture of the styrenic block copolymer or may be separately blended with the styrenic block copolymer as a further technique for achieving a target polystyrene content or modifying the adhesive properties of the composition.

While in prior art adhesive compositions, the use of di-blocks indeed reduced the viscosity, it had several drawbacks, which detracted from its usefulness, that is, it created other problems such as, for example, it made the adhesive compositions less than desirable from the standpoint of elevated temperature resistance. The present invention allows to obtain the desired cohesive strengths, wettability and open times without using di-blocks.

S-B-S, S-V-S and (S-B)n Block Copolymers

Preferred S-B-S, S-V-S and (S-B)n multi-purpose adhesive compositions of the present invention contain about 100 parts of an S-B-S, S-V-S or (S-B)n block copolymer or mixtures thereof (including modified or hydrogenated derivatives) having a styrene content of about 28 to 45% and preferably 43% by weight of the entire block copolymer, about 220 parts of a compatible tackifying resin according to the present invention; about 80 parts of a naphthenic/paraffinic mineral oil; and 0.5 to 4.0 parts of a suitable antioxidant. The S-B-S, S-V-S and (S-B)n block copolymer component of the hot-melt adhesives of the present invention may include:

A block or multi-block copolymer having the general configuration A-B-A or A-B-A-B-A-B- where the elastomeric block (B) is e.g. butadiene or vinyl butadiene and the non-elastomeric block (A) is e.g. styrene. Further, they may be linear or branched. Typical branched structures contain an elastomeric part with at least three branches which can radiate out from a central hub or can be otherwise coupled together. The non-elastomeric blocks, which make up 10% to 80% by weight of the block copolymer may comprise homopolymers or copolymers of vinyl monomers such as vinyl arenes, vinyl pyridines, vinyl halides and vinyl carboxylates, as well as acrylic monomers, such as, acrylonitrile, methacrylonitrile, esters of acrylic acids, etc. Monovinyl aromatic hydrocarbons include particularly those of the benzene series, such as, styrene, vinyl toluene, (alpha)methyl-styrene, vinyl xylene, ethyl vinyl benzene as well as dicyclic monovinyl compounds, such as, vinyl naphthalene and the like. Other non-elastomeric polymer blocks may be derived from alpha olefins, alkylene oxides, acetals, urethanes etc. Styrene is usually preferred as non-elastomeric block.

The elastomeric block component making up the remainder of the copolymer is preferably butadiene or vinyl butadiene, which may or may not be modified or hydrogenated, either partially or substantially complete. Selected conditions may be employed, for example, to hydrogenate the elastomeric block, while not so modifying the vinyl arene polymer blocks. Other conditions may be chosen to hydrogenate substantially uniformly along the polymer chain, both the elastomeric and non-elastomeric blocks thereof being hydrogenated to practically the same extent, which may be either partial or substantially complete.

In the preferred embodiment, the total concentration of styrene in the block copolymer ranges from about 10% to about 80% of the total weight of the copolymer. Suitable styrene-butadiene-styrene block copolymers for use herein are commercially available from the Firestone Rubber & Latex Company under the trade-name "Stereon®".

The preferred block copolymer for use in the compositions of the present invention is "Stereon® 840A". Other commercially available polymers include, for example, those polymers manufactured under the trademarks "Stereon® 857", "Kraton® D-1102CU", "Finaprene® 602", "Finaprene® 417", "Vector® 4261", "Vector® 4461", "Europrene® Sol T 168" and "Europrene® Sol TE 6414". "Kraton®" copolymers are manufactured by Shell Chemical Company; "Finaprene®" copolymers are produced by Fina Oil & Chemical Company; "Vector®" copolymers are manufactured by The Dexco Chemical Company; and "Europrene® Sol T or TE" copolymers are produced by Enichem Chemical Company.

It will also be recognized that mixtures of the above block copolymers, including mixtures of S-B-S, S-V-S, (S-B)n and S-I-S block copolymers, and including any modified and/or hydrogenated derivatives thereof, may also be used as base copolymer components in the adhesives employed for use in manufacturing disposable soft goods.

It should be understood, however, that for S-B-S systems, an adjustment of the range of styrene, that is, the percent weight of the styrene as compared with the total weight of the S-B-S copolymer, below about 28% or above about 45% as specified herein, may produce less favourable results in the above preferred formulation. Adjustment of the percentage of tackifying resin or plasticizing oil may in that case be desirable to obtain a better performance.

As will become evident hereinafter, the inventors of the present invention have discovered particularly surprising results when they employed S-B-S copolymers having as a percentage of the total weight of the copolymers, a styrene content in the range of about 40% or higher. In particular, the inventors have discovered that the hot-melt construction adhesive compositions formulated with tackifying resins according to the present invention display an unusually combination of high cohesive values and low adhesive viscosities in block copolymers having higher styrene contents, in comparison with prior art compositions based on commercially available styrenated polyterpene resins and especially compositions based on rosin esters. This is shown by reference to Examples 9 through 21.

These comparative test results will be discussed in greater detail hereinafter.

The tackifying resins which are used in the hot melt construction adhesives of the present invention have a unique chemical structure in combination with a specific aromatic/aliphatic balance and/or a relatively high polarity. They are tackifying resins which do delay the order-disorder transition of the styrenic block copolymer based adhesive system, but which do not, or only to a limited extent, associate with the styrenic end-blocks of the polymer, that is, at temperatures below approximately 45° C.–50° C. Besides that, the tackifying resin of the present invention have a limited compatibility with the mid-block phase of the styrenic block copolymer, thereby reducing the mobility of the continuous phase of the adhesive, which results in harder adhesives having less tack, but a higher level of cohesion strength, that is, a: temperatures below about 45° C. to 50° C.

As should be understood, the advantageous effects of the present invention are present with all types of styrenic block copolymers, such as, but not limited to, S-I-S, S-B-S, S-V-S and (S-B)n block copolymers, including mixtures thereof and including modified and/or hydrogenated derivatives thereof.

Tackifying Resin Component (b)

The amount of tackifying resin employed in the present invention, is preferably from 20 to 450 parts by weight per hundred parts (phr) styrenic block copolymer, more preferably from 60 to 300 phr, most preferably from 80 to 250 phr.

A suitable tackifying resin in accordance with the present invention can be identified by using an S-I-S reference composition. This reference composition consists of 100 parts by weight of a styrene-isoprene-styrene copolymer having a styrene content of 20 to 30% by weight, 250 parts by weight of said tackifying resin, 50 parts by weight of a paraffinic/naphthenic (70/30) extender oil (Ondina® 7047) and 2 parts by weight of a stabilizer consisting essentially of pentaerythrityl-tetrakis[3-(3,5-di-tert.butyl-4-hydroxyphenyl)-propionate] (Irganox® 1010).

When a tackifying resin according to the present invention is incorporated into this reference composition in the above amount, then the reference composition exhibits the following properties:

it has a tan δ value of about 3.5 or less, wherein tan δ is defined as the ratio between the loss modulus and the storage modulus of said composition;

it shows an elastic retention on spandex fibers (300%) or natural latex rubber (200%) after 4 h at 40° C. of about 70% or more; and it has a crossover temperature of about 95° C. or less;

it exhibits a melt viscosity at 120° C. of about 60,000 mPa.s or less.

The present invention is based on the finding that any thus identifiable tackifying resin provides the surprisingly advantageous effects in a styrenic block copolymer based adhesive composition as described above, irrespective of the exact nature of the styrenic block copolymer component (a) and the other components (c) to (e). In other words, the tackifying resins of the present invention can universally be employed in any styrenic block copolymer based hot-melt adhesive composition with success.

The methods of measuring tan δ, the elastic retention, the adhesive viscosity and the crossover temperature will be described in the Examples and in section Materials & Methods below.

Preferably, the tackifying resin of the present invention has a Ring and Ball softening point of from about 50° C. to about 150° C., more preferably of from about 60° C. to about 140° C., most preferably of from about 95° C. to about 105° C.

Regarding its chemical nature, a "tackifying resin" according to the present invention may include:

(a) natural and modified rosins, such as, for example, gum rosin, wood rosin, tall-oil rosin, distilled rosin, hydrogenated rosin, dehydrogenated rosin, dimerized rosin, polymerized rosin and rosin derivatives of esters of polyhydric alcohols, including polar or otherwise modified rosins;

(b) polyterpene resins generally resulting from the polymerization of terpene hydrocarbons, such as, for example, the mono-terpene known as pinene, in the presence of Friedel-Crafts catalysts at moderately low temperatures;

(c) copolymers and terpolymers of natural terpenes, e.g. styrene/terpene, (alpha) -methyl styrene/terpene and vinyl toluene/terpene;

(d) polar or otherwise modified terpene resins, e.g. phenolic-modified terpene resins such as, for example, the resin product resulting from the condensation, in an acidic medium, of a terpene and a phenol;

(e) aliphatic petroleum hydrocarbon resins, the latter resins resulting from the polymerization of monomers consisting primarily of olefins and diolefins;

(f) aromatic petroleum hydrocarbons;

(g) aliphatic/aromatic petroleum derived hydrocarbons;

(h) polar or otherwise modified aliphatic and/or aromatic petroleum hydrocarbon resins, such as, for example, copolymers and terpolymers of petroleum hydrocarbon resins with vinyl monomers, or mixtures thereof, such as vinyl arenes, vinyl pyridines, vinyl halides and vinyl carboxylates, including particularly those monovinyl aromatic hydrocarbons of the benzene series, such as, styrene, vinyl toluene, (alpha)-methyl-styrene, vinyl xylene, ethyl vinyl benzene, as well as dicyclic monovinyl compounds, such as, vinyl naphtalene and the like, as well as acrylic monomers, such as, acrylonitrile, methacrylonitrile, esters of acrylic acids, etc. Other modifying ingredients may be derived from alpha olefins, alkylene oxides, acetals, urethanes, natural rosins, phenols, etc.

Mixtures of two or more of the above described tackifying resins may be required or advantageous for some formulations. Also included are (preferably partially) hydrogenated or hydrotreated derivatives of the above resins and any mixtures thereof with other (hydrogenated or not hydrogenated, modified or unmodified) resins. Hydrotreated derivatives are derivatives which were subjected to a catalytic treatment as described in U.S. Pat. No. 5,491,214 to Daughenbaugh et al.

Partially hydrogenated aromatic resins are preferred as tackifying resins in the present invention. More preferred are partially hydrogenated C9 aromatic resins. These are available under the trade-name "Regalite® Hydrogenated Hydrocarbon Resin" and "Hercules® MBG Hydrogenated Hydrocarbon Resin" from Hercules B.V. Chemical Company. If desired, resins may be added which improve the elevated temperature resistance of the compound. Such resins should have a tendency to associate with the styrene portion of the polymer.

Particularly suitable for obtaining the beneficial effects of the present invention are partially hydrogenated aromatic hydrocarbon resins having the following properties:

(a) A Ring and Ball softening point of from about 50° C. to about 150° C., more preferably of from about 60° C. to about 140° C, most preferably of from about 75° C. to about 135° C.;

(b) An MMAP cloudpoint of from about 10° C. to about 75° C., more preferably of from about 20° C. to about 70° C.;

(c) A DACP cloudpoint of maximum 35° C., more preferably of maximum 25° C., most preferably of maximum 15° C;

(d) An Mz value of about 10,000 Dalton or less, more preferably of maximum 5,000 Dalton, most preferably of maximum 3,000 Dalton; and (e) A UV absorbance at 268 nm (UV alpha) ranging from 2.0 to 5.0, preferably from 2.7 to 3.1.

Thus, a preferred hot-melt adhesive composition of the present invention should include a tackifying resin which has an R&B value of 60° C. to 140° C., an MMAP of 20° C. to 70° C., a DACP of 25° C. or less; an Mz of 5,000 Dalton or less, and a UV absorbance at 268 nm of 2.7 to 3.1. An even more preferred tackifying resin of the present invention has an R&B value of about 75° C. to 135° C., an MMAP of about. 20° C. to 70° C.; a DACP of about 15° C. or less, an Mz of 3,000 Dalton or less and a UV absorbance at 268 nm (UV alpha) cf 2.7 to 3.1.

The presently most preferred embodiment of the present invention is a partially hydrogenated aromatic C9 hydrocarbon resin having the following properties:

| | |
|---|---|
| R&B softening point (° C.) | 100 ± 5° C., e.g. 102° C. |
| MMAP (° C.) | 52 ± 5° C. |
| DACP (° C.) | 2 ± 5° C. |
| UV-alpha 268 nm | 2.9 ± 0.2 |
| Mz (Dalton) | 1,500 ± 30% |

In the following, a partially hydrogenated aromatic C9 hydrocarbon resin having the above properties will be designated as Inventive Resin, abbreviated RESIN I.

The above mentioned partially hydrogenated aromatic tackifying resins which can be used in the hot-melt adhesives of the present invention may be produced by polymerization and subsequent hydrogenation of an unsaturated aromatic feedstream. The feedstream from which the resins are made predominantly contains monomers having 7 to 10 carbon atoms. The resin feedstream typically includes styrene, alpha-methylstyrene, vinyl toluenes, indene and alkyl-substituted indenes as reactive compounds and is polymerized using a suitable Friedel-crafts catalyst system. It is possible and economically advantageous to use a hydrocarbon feedstream as obtained as a by-product from naptha cracking plants. A preferred typical C9 feedstream may contain the following main components:

| | |
|---|---|
| styrene | 3% |
| alpha-methylstyrene | 4% |
| vinyl toluene | 20% |
| indene | 22% |
| alkyl substituted indenes | 6% |
| related homologues | 3% |
| trimethyl benzene | 10% |
| ethyl toluene | 15% |
| naphthalene | 2–5% |
| dicyclopentadiene (DCPD) | <1% |

The polymerization catalyst can be a suitable Friedel-Crafts-catalyst and is not particularly critical. Use can be made of $BF_3$, $AlBr_3$, $AlF_3$ and $AlCl_3$ and complexes thereof as catalytic components. Aluminium chlorides and/or complexes thereof are most preferred.

We have found that resins having the above desirable combination of properties can be obtained by hydrogenation of petroleum resins obtainable by polymerization of the mentioned aromatic feedstreams. The above preferred embodiment of this invention is, inter alia, based on the finding that the degree of hydrogenation of the aromatic rings is important to achieve the desired compatibility with the other components of the adhesive systems. Generally, a lower degree of hydrogenation as conventionally used brings about advantageous effects. The hydrogenation may be performed in a batch or continuous process.

Hydrogenation catalysts can be selected from the metals of Groups VIII, VIB, IB and IIB of the Periodic Table and oxides thereof. These metals or their oxides can be used alone or in combination. The metals or metal oxides can be used directly or can be carried on a suitable support such as silica, alumina, or carbon. Nickel/zinc oxide on a silica support is most preferred.

The hydrogenation step may take place in a solution of the resin in a suitable hydrocarbon solvent. The hydrogenation is carried out with a hydrogen pressure of 20 to 300 bar, preferably 75 to 175 bar. A suitable reaction temperature range is about 200° C. to 300° C., preferably 250° C. to 280° C. The hydrogenation time usually varies from ¼ to 2 hours, preferably about 20 minutes to 1 hour.

Most preferred conditions involve the use of a Ni/ZnO catalyst under a hydrogen pressure of 75 to 175 bar and a temperature of 250–270° C. during 20 minutes to 1 hour.

When the resins to be hydrogenated are made by polymerizing monomers in the presence of a chlorine containing catalyst, the resins are dechlorinated to prevent the hydrogenation catalyst from deactivation.

The resin feedstock is hydrogenated to a level where the resultant resin has a UV alpha value at 268 nm ranging from 2.0 to 5.0, preferably from 2.7 to 3.1, and the appropriate MMAP and DACP values to obtain the desired properties. Thus, in this preferred embodiment the degree of hydrogenation is a means to control the properties of the resulting tackifying resin and the adhesive containing same.

Following hydrogenation the resin can be isolated by conventional stripping techniques followed by steam sparge.

The resultant resins have a molecular weight (Mz) as measured by GPC of about 10,000 or less, preferably of 3,000 or less.

Plasticizing Oil Component (c)

Various plasticizing oils or extending oils also may be present in the adhesive composition of the present invention in amounts of about 0 to about 150 parts, preferably from about 5 to about 150 parts, and most preferably from about 25 to about 100 parts in order to provide or improve the wetting action and/or viscosity control. Commercially available plasticizing oils include, for example, those manufactured under the trademarks, "Shellflex®", "Ondina®" (both produced by Shell Chemical Company), "Primol®", "Flexon®" (Exxon Chemical Company), or "Kaydol®" (Witco Chemical Company).

The plasticizing oils include not only the usual plasticizing oils, but also naphthenic/paraffinic oils, olefin oligomers and low molecular weight polymers, as well as vegetable and animal oil and derivatives of such oils. Plasticizer oils also include liquid resins as well as mixtures thereof with olefin oligomers and/or low molecular weight polymers. The plasticizer oils may also be hydrogenated versions thereof. The petroleum derived oils which may be employed are relatively high boiling temperature materials containing only a minor proportion of aromatic hydrocarbons. In this regard, the aromatic hydrocarbons should preferably be less than 30%, and more particularly less than 15%, by weight, of the oil. Alternatively, the oil may be totally non-aromatic.

Liquid resin of use in this invention may be any resin having a R&B softening point below the R&B softening point of the tackifying resin of this invention. Preferably the liquid resin should have a R&B softening point below 50° C., most preferably, the liquid resin has e R&B softening point below ambient temperature (21° C.).

The oligomers may be polypropylenes, polybutenes, hydrogenated polyisoprene, hydrogenated butadiene, or the like having average molecular weights between about 350 Dalton and about 10,000 Dalton. Commercially available plasticizing oligomers include, for example, those manufactured under the trademarks, "Napvis®", "Hyvis®", which are both manufactured by BP Chemical Company, or "Amoco Polybutenes®", manufactured by the Amoco Chemical Specialities Company. Suitable vegetable and animals oils include glycerol esters of the usual fatty acids and polymerization products thereof.

Small amounts of petroleum derived waxes may be used as well to control or reduce the melt viscosity of hot-melt construction adhesives, without appreciably decreasing their adhesive bonding characteristics. As should be understood, each of these wax diluents is solid at room temperature. Among the useful wax gum diluents are:

(1) Low molecular weight, that is, 1000–6000, polyethylene having a hardness value, as determined by ASTM method D-1321, of from about 0.1 to 120 and ASTM softening points of from about 65° C. to 125° C.;

(2) Petroleum waxes such as paraffin wax having a melting point of from about 55° C. to 100° C. and microcrystalline wax having a melting point of from about 55° C. to 100° C., the latter melting points being determined by ASTM method D127-60;

(3) Atactic polypropylene having a Ring and Ball softening point of from about 120° C. to 160° C.;

(4) Synthetic waxes made by polymerizing carbon monoxide and hydrogen such as Fischer-Tropsch wax.

Commercially available waxes include, for example, those manufactured under the trademarks, "Polywax®" and "Ultraflex®", both manufactured by Petrolite Polymers Chemical Company; "Sasolwaks®", produced by Sch ümann Sasol Chemical Company; "Epolene®", manufactured by Eastman Chemical Company; and "Escomer®", produced by Exxon Chemical Company. Other useful substances include hydrogenated animal, fish and vegetable fats and oils such as hydrogenated tallow, lard, soya oil, cottonseed oil, castor oil, menhadin oil, cod liver oil, etc., and which are solid at ambient temperature by virtue of their being hydrogenated, have also been found to be useful with respect to functioning as a wax diluent equivalent.

These hydrogenated materials are often referred to in the adhesives industry as "animal or vegetable waxes". Additionally, hydrocarbon oils, especially naphthenic or paraffinic process oils, may also be employed herein as the wax diluent. Optionally, these materials may be incorporated into the adhesive composition of the present invention in the form of a coating to improve the handling characteristics of the adhesive composition.

Stabilizer Component (d)

Optional components of the present invention are stabilizers which inhibit or retard heat degradation, oxidation, skin formation and color formation. Stabilizers are typically added to the commercially available compounds in order to protect the compositions against heat degradation and oxidation during the preparation, and high-temperature storage of the adhesive composition. Additional stabilizers known in the art may also be incorporated into the adhesive composition. These may be for protection during the life of the disposable article against, for example, oxygen, ozone and ultraviolet radiation.

The stabilizers which can be used in the hot melt adhesive compositions of the present invention are incorporated to help protect the otherwise vulnerable styrenic block copolymer and thereby the total adhesive composition, from a deleterious thermal and oxidative degradation which is frequently experienced by other similar copolymers during the manufacture and application of adhesive compositions utilizing same, as well as in the ordinary use of the final manufactured product. As should be understood, such degradation usually manifests itself by the deterioration of the adhesive composition in appearance, physical properties and performance.

Among the most useful stabilizers are high molecular weight hindered phenols and multifunctional phenols, such as sulfur and phosphorous-containing phenols. In this regard, hindered phenols are known to those skilled in the art and may be characterized as phenolic compounds which also contain sterically bulky radicals in close proximity to the phenolic hydroxyl group thereof.

In particular, tertiary butyl groups generally are substituted onto the benzene ring in at least one of the ortho positions relative to the phenolic hydroxyl group. The presence of these sterically bulky substituted radicals in the vicinity of the hydroxyl group is believed to retard its stretching frequency and correspondingly, its reactivity. This steric hindrance is believed to provide the phenolic compounds with its stabilizing properties. Representative hindered phenols include:

1,3,5-trimethyl-2,4,6-tris(3,5 di-tert.butyl-4-hydroxybenzyl) benzene;

pentaerythritol tetrakis-[3(3,5 di-tert.butyl-4-hydroxyphenyl) propionate];

n-octadecyl-3-(3,5-di-tert.butyl-4-hydroxyphenyl) propionate;

4,4'-methylenebis (4-methyl-6-tert butylphenol);

4,4'-thiobis(6-tert-butyl-o-cresol);

2,6-di-tert-butylphenol;

6-(4-hydroxyphenoxy)-2,4-bis(n-octylthio)-1,3,5-triazine;

2,4,6-tris(4-hydroxy-3,5-di-tert-butyl-phenoxy)-1,3,5-triazine;

di-n-octadecyl-3,5-di-tert-butyl-4-hydroxybenzylphosphonate;

2-(n-octylthio)ethyl-3,5-di-tert-butyl-4-hydroxy-benzoate; and sorbitol hexa-[3,3,5-di-tert-butyl-4-hydroxy-phenyl) propionate].

Especially preferred as a stabilizer is pentaerythritol tetrakis-[3-(3,5-di-tert-butyl-4-hydroxyphenyl) propionate].

The performance of these stabilizers may be further enhanced by utilizing, in conjunction therewith;

(1) synergists such as, for example, thiodipropionate esters and phosphites; and (2) chelating agents and metal deactivators as, for example, ethylenediaminetetraacetic acid, salts thereof, and disalicylpropylenediimine.

Commercially available stabilizers include, for example, those manufactured under the trademarks, "Irganox®", "Naugard®", "Anox®", and "Ultranox®". These stabilizers are manufactured by respectively Ciba-Geigy Chemical Co.; Uniroyal Chemical Co.; Enichem Chemical Co.; and General Electric Chemical Co.

These stabilizers, if used, are generally present in amounts of >0 to about 4, preferably about 0.1 to about 4, more preferably about 0.2 to 1.5 percent, and most preferably 0.25% to 1.0%.

Preparation of the adhesive composition of the present invention:

All adhesive compositions of the present invention can be prepared by blending the components at an elevated temperature, preferably between 130° C. and 200° C., until a homogeneous blend is obtained, for usually less than three hours. Various methods of blending are known and any method that produces a homogeneous blend is satisfactory.

A representative example of such a procedure involves placing all of the oil and stabilizer substances in a jacketed mixing kettle, and preferably in a jacketed heavy duty mixer of the Baker-Perkins or Day type, which is equipped with rotors, and thereupon raising the temperature of this mixture to a range of from about 120° C. to 180° C. As should be understood, the precise temperature to be used in this step will depend on the melting point of the particular ingredients. When the initial mixture, noted above, has been heated, the mixture is blanketed in $CO_2$ at a slow flow rate and the resins described above, are slowly added. When the resins are molten, and at the desired temperature, the block copolymer is added to the mixture. The resultant adhesive composition mixture is agitated until the block copolymer is completely dissolved. A vacuum is then applied to remove any entrapped air. Optional additives may be incorporated into the hot melt construction adhesive compositions in order to modify particular physical properties. These additives may include, colorants, such as titanium dioxide; and fillers such as talc and clay, etc.

Properties and usage of the Adhesives of the Present Invention:

The styrenic block copolymer based hot-melt adhesives employing the tackifying resins of the present invention have a low viscosity, excellent application characteristics and are well suited for multi-purpose use as construction or elastic attachment adhesives, or both.

The resultant adhesives may thus be used in a wide variety of product assembly applications, mainly in the diapers or feminine napkins production. A particularly preferred application is their use in bonding lightweight materials such as, but not limited to, polyethylene or polypropylene substrates to paper, fabric, tissue, non-wovens, polyethylene or polypropylene substrates, or to themselves. An additional advantage of the adhesive of the present invention is that it can be effectively applied by spray or wheel application systems or multi-bead or slot extrusion. The hot-melt adhesive compositions are particularly well-suited for spray applications.

The hot-melt adhesive compositions of the present invention contain a tackifying resin which delays the order-disorder transition of the styrenic block copolymer based adhesive system, but does not, or only to a limited extent, associate with the styrenic end-blocks of the polymer, that is, at temperatures below approximately 45° C.–50° C. Besides that, the tackifying resin of the present invention has only a limited compatibility with the mid-block phase of the styrenic block copolymer. Thus, it can impart the advantageous adhesive and cohesive properties to a hot-melt adhesive composition containing same as described above.

The invention is further illustrated by way of the following examples.

EXAMPLES

All examples containing compositions based on S-I-S block copolymers are formulated according to the general composition:

| | |
|---|---|
| S—I—S copolymer | 100 parts |
| Tackifying Resin | 250 parts |
| Ondina ® 7047 (paraffinic/naphthenic oil) | 50 parts |
| Irganox ® 1010 (stabilizer) | 2 parts |

This general composition is also useful as a reference composition to identify a useful tackifying resin according to the present invention provided that its styrene content ranges from 20 to 30%.

All examples containing compositions based on S-B-S, S-V-S or (S-B)n block copolymers are formulated according to the following general composition:

| | |
|---|---|
| Polymer | 100 parts |
| Tackifying Resin | 220 parts |
| Ondina ® 7047 | 80 parts |
| Irganox ® 1010 | 2 parts |

Examples 1 to 8 illustrate the effects of varying the properties of the tackifying resin on the adhesive properties and the Theological behavior of a standard S-I-S based hot-melt adhesive. Examples 9 to 21 illustrate the effects of varying the properties of the tackifying resin on the adhesive properties and rheological behavior of a standard S-B-S, S-V-S or (S-B)n based hot-melt adhesive.

The resin developed according to this invention is generally called RESIN I as mentioned above. Further abbreviations and materials as well as the methods of measuring the properties listed in the tables will be explained in the section Materials & Methods below.

In tables 1 to 21, the first block of figures relates to some properties of the tackifying resin used (such as R&B, MMAP, DACP and the like), while the remainder relates to properties measured in the final hot-melt adhesive composition.

Example 1

Table 1 shows the effect of the degree of hydrogenation of a preferred group of tackifying resins on the properties of the resin and on the performance of S-I-S based hot-melt adhesives containing Europrene® Sol T 193B as the sole polymer. Resins with a decreasing degree of hydrogenation exhibit an increasing content of aromatic structures indicated by increasing UV-alpha values and reduced MMAP cloudpoints. The results show an increase in resin functionality, indicated by lower DACP cloudpoints, with decreasing levels of hydrogenation.

As indicated earlier certain tackifying resins are able to delay the order-disorder transition process of the polymer, especially those containing a certain amount of polar or aromatic components. The results of table 1 indicate clearly that resins with a lower degree of hydrogenation appear to postpone the significant increase in adhesive viscosity, caused by the mid-block and end-block phase segregation. The delay in the order-disorder transition of the styrene end-blocks of the polymer is demonstrated by an explicit decrease in adhesive viscosity, especially at lower temperatures such as 120° C., for compositions containing resins having decreasing MMAP cloudpoints and increasing UV-alpha values; as well as lower SAFT and 70° C. shear values, which indicate an increasing mobility of the end-blocks at temperatures above about 45–50° C. It also became evident following the experiments of table 1 that the selected hydrogenated C9 resin samples did not associate with the styrenic end-blocks of the block copolymer at temperatures below approximately 45–50° C., that is, they completely associate with the isoprene mid-blocks of the block copolymer at these temperatures. The test results indicate an increasing hardness, thus a reduced mobility of the adhesive, with decreasing levels of resin hydrogenation. An association of the resin with the end-block domains of the polymer would have increased the mobility of the system. Lower peel, loop tack, and needle penetration values for higher UV-alpha resins demonstrate the increasing hardness of the adhesive composition. A decreasing degree of resin hydrogenation also reduces the compatibility of the resin with the isoprene mid-blocks of the polymer, which results in a higher cohesive strength of the continuous phase of the compounded S-I-S adhesive system. Increasing shear values for higher UV-alpha resins at room temperature and at 40° C. clearly indicate this behavior.

Example 2

Because of the requirements for nonwoven hot-melt adhesives, described in the prior art, and according to the results of table 1, laboratory sample C, having a UV-alpha value around 3, and the lowest viscosity at 120° C., was regarded to have the best balance of properties. A novel development resin according to the properties of this preferred sample C was produced on a larger (plant-trial) scale. This is RESIN I.

Table 2 shows the effect of RESIN I in comparison with several commercially available tackifying resins, which possess a lower functionality, on the performance of S-I-S based hot-melt adhesives containing Kraton® D-KX 602CS as the sole polymer.

The results clearly indicate the best balanced adhesive performance for the system based on RESIN I, both at low and high temperatures.

To obtain hot-melt adhesives with superior wettability, adhesion, and long open-times, the system should have a high degree of mobility at temperatures above about 45° C.–50° C., that is, especially at those temperatures at which the adhesive bond is established: from about 80° C. to about 120° C. Lower adhesive viscosities, especially at 120° C., lower SAFT and shear properties, that is, at temperatures above about 45° C.–50° C., and a lower adhesive softening point usually indicate a higher degree of mobility for the system at the above mentioned temperatures. In this respect, the results from table 2 show the best performance for systems based on RESIN I or ECR® 179A.

At temperatures below approximately 45° C.–50° C., preferably, the tackifying resin should not associate anymore with the styrenic end-blocks of the block copolymer, that is, it would be highly benificial for the cohesive properties of the system when the resin only associates with the isoprene mid-blocks of the block copolymer at these temperatures. Moreover, the cohesion of the system would increase, when the compatibility of the resin with the polymer mid-block would be decreased to some extent, thereby reducing the mobility of the continuous phase of the adhesive. Lower peel values, loop tack values and needle penetration values indicate an increasing hardness, thus a reduced mobility of the adhesive system at room temperature. A higher cohesion of: the system, at temperatures below approximately 45° C.–50° C., is illustrated by higher shear values at 23° C., 40° C., and 45° C.

In this respect, the test results from table 2 clearly indicate the superior performance of the systems based on RESIN I and Regalite® S 260 Hydrogenated Hydrocarbon Resin. Although ECR® 179A shows good performance at high temperatures, it increases the mobility of the system at temperatures below about 45° C.–50° C. to a much higher extent than, for example Regalite® S 260 Hydrogenated Hydrocarbon Resin, and especially RESIN I. According to these results RESIN I appears to be the best resin to decrease the viscosity of hot-melt adhesive compositions which employ S-I-S block copolymers, or mixtures thereof, without a simultaneous loss of cohesive strength, either at ambient temperatures or elevated temperatures, that is, temperatures up to about 45° C.–50° C.

Example 3

Table 3 shows the effect of RESIN I in comparison with several commercially available tackifying resins, which possess a lower functionality, on the performance of S-I-S based hot-melt adhesives containing Europrene® Sol T 193B as the sole polymer. Like in Example 2 the results clearly indicate the best balanced adhesive performance for the system based on RESIN I, both at low and high temperatures.

Example 4

Table 4 displays the effect of RESIN I in comparison with several commercially available tackifying resins, which possess a lower functionality, and one laboratory resin sample (Sample F), having a higher functionality, on the application performance of S-I-S based hot-melt adhesives containing Kraton® D-KX 602CS as the sole polymer. The adhesives were all sprayed onto PE using a Nordson controlled fiberization unit (add on level approximately 20 g/cm²) and bonded to standard nonwoven material. Lycra® and Natural rubber latex elastic attachments were made using the same technique.

Superior adhesive performance is symbolized by high PE-nonwoven peel values and a low percentage of creep, i.e. a high percentage of elastic retention. The results indeed indicate a superior creep performance for the systems based on resins possessing a higher functionality, such as RESIN I and Sample F. The adhesive based on RESIN I clearly exhibits the best peel results. The PE-nonwoven bond was so strong (>9) that both substrates were completely disrupted.

Example 5

Table 5 shows the effect of RESIN I in comparison with several commercially available tackifying resins, which are lower, equal, and higher in functionality, on the performance of S-I-S based hot-melt adhesives containing Europrene® Sol T 193B as the sole polymer. Although the systems based on Piccolyte® HM 106 Synthetic Resin and Permalyn® 6110 Rosin Ester respectively exhibit an equal and higher functionality compared with RESIN I, the results clearly demonstrate the best balanced adhesive performance for the system based on RESIN I, both at low and high temperatures.

Systems based on Piccolyte® HM 106 Synthetic Resin exhibit too high viscosities at 120° C. to ensure perfect wettability. Compositions based on Permalyn® 6110 Rosin Ester exhibit low viscosities and good wettability at high temperatures, but their cohesion performance below temperatures of about 45° C.–50° C., is clearly inferior compared with the adhesive based on RESIN I. Also in comparison with the other resins, the results clearly indicate superior adhesive performance for the system based on RESIN I.

Example 6

Table 6 illustrates the effect of RESIN I in comparison with Regalite® S 260 Hydrogenated Hydrocarbon Resin, which is somewhat lower in functionality, on the performance of hot-melt adhesives based on four different S-I-S block copolymers, which mainly differ in percentage of styrene. Due to its unique chemical structure RESIN I is more able to delay the order-disorder transition of the styrene end-blocks of the polymer, than is Regalite® S 260 Hydrogenated Hydrocarbon Resin. This effect is clearly illustrated by the lower SAFT values, lower shear values at 70° C., and especially the significantly lower viscosities at 120° C. of the systems based on RESIN I.

The above mentioned differences appear to be more apparent for systems based on higher styrene content polymers. The results of table 6 display a superior adhesive performance for systems based on RESIN I. Lower peel values, loop tack values and needle penetration values for the system based on RESIN I indicate a harder adhesive, having a reduced mobility and thus a higher cohesion at temperatures below 45–50° C.

Examples 7 & 8

Rheological evaluations

Dynamic Mechanical Analysis (DMA) is a convenient method of quantifying the mobility and end-block solidity in terms of visco-elastic behavior of hot-melt adhesives. The results of a dynamic mechanical analysis of hot-melt adhesives can be displayed in rheological diagrams which may help to illustrate, in three different curves (G', G" and Tan δ), the visco-elastic behavior of the system.

Tan δ is the ratio between G", the loss modulus of the system (i.e. the measure of viscous strength, or the ability to dissipate deformation as viscous motion), and. G', the storage modulus of the system (i.e. indicating strength, hardness and elastic memory) and reflects the balance of visco-elastic behavior. With this technique an impression can be obtained of the interaction between resin and elastomer over a wide temperature range.

Especially at those temperatures where the final bond must perform well, that is, from about 0° C. up to about 45° C.–50° C., it was found that higher G' values and lower tan δ peak values correspond to a reduced mobility, symbolizing a harder adhesive, exhibiting a lower degree of tack and higher cohesive strength. It was further found that the cross-over temperature between G' and G" (tan δ=1) can be used to evaluate the adhesive viscosity at high temperatures. Lower cross-over temperatures indicate longer open-times and better wettability characteristics.

Tables 7 and 8 show the effect on the rheological performance of adhesives based on RESIN I in comparison with systems based on several commercially available tackifying resins, which are lower, equal, and higher in functionality.

The rheological performance of these resins is compared in two different S-I-S based hot-melt adhesives, containing, respectively, Kraton® D-KX 602CS and Europrene® Sol T 193B as the sole polymer.

Although the systems based on Piccolyte® HM 106 Synthetic Resin, Permalyn® 6110 Rosin Ester, ECR® 368LC, respectively exhibit a similar or higher functionality compared with RESIN I, the results clearly demonstrate the best balanced adhesive performance for the system based c)n RESIN I, both at low and high temperatures.

The adhesives based on Piccolyte® HM 106 Synthetic Resin, ECR 368LC and the Regalite® Hydrogenated Hydrocarbon Resins exhibit a higher cross-over temperature and their G' values at temperatures below about 45° C.–50° C. are clearly lower compared with the adhesive based on RESIN I. Lower G' values can also be found for the systems based on Permalyn® 6110 Rosin Resin and ECR® 179A.

Also the significantly lower tan δ peak value of the RESIN I system, together with its higher tan δ peak temperature, lead to a lower mid-block compatibility for this resin, that is, a reduced mobility of the continuous phase of the adhesive, which manifests itself in a higher cohesive strength for the system.

Moreover, in comparison with the other resins, the results explicitly display a superior and best balanced adhesive performance for the hot-melt systems based on RESIN I.

Example 9

Table 9 shows the effect of RESIN I in comparison with several commercially available tackifying resins, which possess a lower, equal, or higher functionality, on the performance of (S-B)n based hot-melt adhesives containing Stereon® 840A as the sole polymer.

Although the systems based on Piccolyte® HM 106 Synthetic Resin and Permalyn® 6110 Rosin Ester respectively exhibit a similar or higher functionality compared with RESIN I, the results explicitly demonstrate a superior adhesive performance for the system based on RESIN I, both at low and high temperatures.

The composition based on Piccolyte® HM 106 Synthetic Resin exhibits a too high viscosity at 120° C. to ensure superior wettability. The system based on Permalyn® 611C Rosin Ester exhibits low viscosities and good wettability at high temperatures, but its cohesion performance below temperatures of about 45° C.–50° C., is lower compared with the adhesive based on RESIN I. Furthermore, the lower needle penetration value of the adhesive based on RESIN I indicates a harder adhesive having a higher level of cohesion at temperatures below 45–50° C. Also in comparison with the other resins, the results clearly indicate the best balanced adhesive performance for the system based on RESIN I.

Example 10

Table 10 shows the effect of RESIN I in comparison with several commercially available tackifying resins, which possess a lower functionality, on the performance of S-V-S based hot-melt adhesives containing Stereon® 857 as the sole polymer. A comparison of the performance of RESEN I with resins having an equal and higher functionality in Stereon® 857 systems is listed in table 16.

The system based on RESIN I exhibits the lowest viscosities, indicating good wettability at high temperatures, and its cohesion performance below temperatures of about 45° C.–50° C., illustrated by higher shear values, is mostly higher compared with the adhesives based on the other Regalite® Hydrogenated Hydrocarbon Resins. The adhesive based on RESIN I also exhibits the lowest needle pentration value, which indicates a harder adhesive at room temperature, having a higher level of cohesive strength.

The results clearly indicate the best balanced adhesive performance for the system based on RESIN I.

Example 11

Table 11 shows the effect of RESIN I in comparison with several commercially available tackifying resins, which possess a lower, equal, or higher functionality, on the performance of S-B-S based hot-melt adhesives containing Europrene® Sol TE 6414 as the sole polymer.

Although the systems based on Piccolyte® HM 106 Synthetic Resin and Permalyn® 6110 Rosin Ester respectively exhibit an equal and higher functionality compared with RESIN I, the results explicitly demonstrate a best balancedadhesive performance for the system based on RESIN I, that is, both at low and high temperatures.

The system based on Piccolyte® HM 106 Synthetic Resin possesses significantly higher viscosities at 120° C. and less wettability. The other compositions exhibit low viscosities and good wettability at high temperatures, but except Piccolyte® HM 106 Synthetic Resin, the cohesion performance below temperatures of about 45° C.–50° C., is clearly lower compared with the adhesive based on RESIN I. The adhesive composition based on RESIN I again shows the lowest needle penetration value.

Also in comparison with the other resins, the results clearly indicate the best balanced adhesive performance for the system based on RESIN I.

Example 12

Table 12 illustrates the effect of RESIN I in comparison with Regalite® S 260 Hydrogenated Hydrocarbon Resin, which is somewhat lower in functionality, on the performance of hot-melt adhesives based on four different S-B-S block copolymers, which mainly differ in percentage of styrene.

Due to its unique chemical structure RESIN I is more able to delay the order-disorder transition of the styrene endblocks of polymer, than is Regalite® S 260 Hydrogenated Hydrocarbon Resin. This effect is clearly illustrated by the lower SAFT values, lower shear values at 70° C., and the mostly lower viscosities at 120° C. of the systems based on RESIN I. At temperatures below approximately 45° C.–50° C., RESIN I also appears to exhibit superior adhesive performance. This is explicitly demonstrated by the lower loop tack values and the higher shear values at 23° C. and 40° C. for the systems based on RESIN I. The above mentioned differences appear to be more apparent for systems based on higher styrene content polymers. The results of table 12 display the best balance in adhesive performance for systems based on RESIN I.

Examples 13, 14, 15 & 16

Rheological evaluations

Tables 13, 14, 15 and 16 show the rheological performance of adhesives based on RESIN I in comparison with systems based on several commercially available tackifying resins, which are lower, equal, and higher in functionality. The Theological performance of these resins is compared in three different S-B-S based hot-melt adhesives and one S-V-S composition, containing, respectively, Stereon® 840A, Europrene® Sol T 168, Finaprene® 417, and Stereon® 857 as the sole polymer.

Although the systems based on Piccolyte® HM 106 Synthetic Resin and Permalyn® 6110 Rosin Ester respectively exhibit a similar or higher functionality compared with RESIN I, the results explicitly demonstrate the best balanced adhesive performance for the system based on RESIN I, both at low and high temperatures.

The adhesives based on Piccolyte® HM 106 Synthetic Resin and the Regalite® Hydrogenated Hydrocarbon Resins exhibit a higher cross-over temperature and their G' values at temperatures below about 45° C.–50° C. are clearly lower compared with the adhesive based on RESIN I. Lower G' values can also be found for the systems based on Permalyn® 6110 Rosin resin.

Having a significantly lower tan δ peak value, the RESIN I system shows a reduced mobility of the continuous phase of the adhesive, which manifests itself in a higher cohesive strength for the system. Moreover, in comparison with the other resins, the results explicitly display a superior and best balanced adhesive performance for the hot-melt systems based on RESIN I.

TABLE 1

Effect of degree of hydrogenation
(S-I-S Polymer: Europrene ® Sol T 193B)
Feeds: Partially hydrogenated aromatic C9 resins.

| Sample: | A | B | C | D | E |
|---|---|---|---|---|---|
| MDSP (° C.) | 105.4 | 105.9 | 106.4 | 106.0 | 106.8 |
| R & B spt. (° C.) calc. | 98.6 | 99.0 | 99.5 | 99.1 | 99.9 |
| UV-alpha 268 nm | 1.03 | 1.99 | 3.17 | 4.02 | 5.06 |
| MMAP (° C.) | 70 | 61 | 51 | 40 | 30 |
| DACP (° C.) | 30 | 14 | −2 | −18 | −24 |
| Color (Gardner) | 0.1 | 0.1 | 0.3 | 1.1 | 2.6 |

TABLE 1-continued

Effect of degree of hydrogenation
(S-I-S Polymer: Europrene ® Sol T 193B)
Feeds: Partially hydrogenated aromatic C9 resins.

| Sample: | A | B | C | D | E |
|---|---|---|---|---|---|
| Peel adhesion (N/25 mm) | | | | | |
| to Steel (23° C.) | 30.4 | 33.3 | 10.0 | 2.6 | # |
| to PE (23° C.) | 6.3 | 7.0 | 1.1 | 0.1 | # |
| Loop tack (N/25 mm) | | | | | |
| to Steel (23° C.) | 45.4 | 38.5 | 12.2 | 0 | # |
| to PE (23° C.) | 20.2 | 6.9 | 3.0 | 0 | # |
| Needle Penetration (23° C., dmm) | 105 | 98 | 65 | 23 | 11 |
| Shear to steel (minutes) | | | | | |
| (23° C., 2.5 kg) | 2,142 | 6,926 | 18,192 | >20,000 | # |
| (40° C., 2.5 kg) | 106.5 | 247.2 | 301.2 | 118.8 | # |
| (70° C., 0.5 kg) | 96 | 51 | 23 | 27 | # |
| Shear to PE (minutes) (40° C., 1 kg) | 2,585 | 2,080 | 9,323 | 7,457 | # |
| SAFT (0.5 kg, ° C.) | 83 | 78 | 72 | 71 | # |
| Viscosity (mPa · s) at: | | | | | |
| 180° C. | 1,890 | 2,060 | 2,150 | 2,240 | 2,180 |
| 160° C. | 4,050 | 4,100 | 4,550 | 4,590 | 4,410 |
| 140° C | 13,800 | 10,700 | 11,250 | 11,280 | 11,300 |
| 120° C. | 57,000 | 39,600 | 37,850 | 39,800 | 40,200 |

: Adhesive was not coated and could not be tested like a tape, because the adhesive composition was too hard and possessed insufficient tack at room temperature.

TABLE 2

Adhesive performance of five different resins
(S-I-S Polymer: Kraton ® D-KX 602CS)

| Tackifying Resin | Regalite ® R 101 | Regalite ® S 101 | Regalite ® S 260 | RESIN I | ECR ® 179A |
|---|---|---|---|---|---|
| R & B spt. (° C.) | 98.9 | 99.1 | 100.4 | 102.8 | 101.5 |
| UV-alpha 268 nm | 0.35 | 0.68 | 2.30 | 2.87 | 1.66 |
| MMAP (° C.) | 79 | 73 | 66 | 54 | 49 |
| DACP (° C.) | 42 | 38 | 17 | 2 | 33 |
| Peel adhesion (N/25 mm) | | | | | |
| to Steel (23° C.) | 32.8 | 34.3 | 36.2 | 17.3 | 33.6 |
| to PE (23° C.) | 7.8 | 6.9 | 7.0 | 4.1 | 9.1 |
| Loop tack (N/25 mm) | | | | | |
| to Steel (23° C.) | 43.2 | 43.2 | 21.1 | 17.8 | 23.0 |
| to PE (23° C.) | 12.1 | 9.0 | 7.8 | 1.4 | 11.4 |
| Needle Penetration (23° C., dmm) | 104 | 102 | 97 | 73 | 97 |
| Shear to steel (minutes) | | | | | |
| (23° C., 2.5 kg) | 2,406 | 2,521 | >81,500 | >88,000 | 8,202 |
| (40° C., 2.5 kg) | 137 | 125 | 269 | 651 | 145 |
| (45° C., 1.0 kg) | 2,459 | 6,237 | >50,000 | 33,201 | 12,515 |
| (50° C., 1.0 kg) | 1,466 | 1,834 | 10,574 | 975 | 676 |
| (60° C., 0.5 kg) | 7,953 | >20,000 | 1,562 | 206 | 132 |
| (70° C., 0.5 kg) | 290 | 206 | 62 | 37 | 31 |
| Shear to PE (minutes) | | | | | |
| (40° C., 1 kg) | 4,304 | 10,855 | 39,617 | 44,664 | 41,000 |
| SAFT (0.5 kg,° C.) | 88 | 86 | 80 | 77 | 70 |
| R & B spt. (° C.) (of adhesive) | 108.4 | 103.8 | 94.1 | 90.1 | 90.4 |
| Viscosity (mPa · s) at: | | | | | |
| 180° C. | 2,020 | 2,050 | 2,290 | 2,280 | 2,580 |
| 160° C. | 4,350 | 4,360 | 4,730 | 4,850 | 5,040 |
| 140° C. | 13,900 | 12,540 | 12,980 | 13,000 | 12,360 |
| 120° C. | 126,000 | 76,400 | 49,400 | 46,500 | 38,500 |

TABLE 3

Adhesive performance of four different resins
(S-I-S Polymer: Europrene ® Sol T 193B)

| Tackifying | Regalite ® | Regalite ® | Regalite ® | RESIN I |
|---|---|---|---|---|
| Resin | R 101 | S 101 | S 260 | |
| R & B spt. (° C.) | 100.5 | 101.0 | 101.7 | 102.8 |
| UV-alpha 268 nm | 0.32 | 0.65 | 2.29 | 2.87 |
| MMAP (° C.) | 80 | 74 | 61 | 54 |
| DACP (° C.) | 47 | 38 | 18 | 2 |
| Peel adhesion (N/25 mm) | | | | |
| to Steel (23° C.) | 26.5 | 29.8 | 23.4 | 6.5 |
| to PE (23° C.) | 6.4 | 6.6 | 4.2 | 0.9 |
| Loop tack (N/25 mm) | | | | |
| to Steel (23° C.) | 53.0 | 28.3 | 31,2 | 8.6 |
| to PE (23° C.) | 1.8 | 2.4 | 6.1 | 0.2 |
| Needle Penetration (23° C., dmm) | — | — | 85 | 69 |
| Shear to steel (minutes) | | | | |
| (23° C., 2.5 kg) | 3480 | 3530 | >10,000 | >10,000 |
| (40° C., 2.5 kg) | 94 | 92 | 377 | 225 |
| (70° C., 0.5 kg) | 264 | 149 | 57 | 45 |
| Shear to PE (minutes) | | | | |
| (40° C., 1 kg) | — | — | 4,309 | 6,699 |
| SAFT (0.5 kg, ° C.) | 83 | 85 | 78 | 73 |
| Viscosity (mPa.s) at: | | | | |
| 180° C. | 2,080 | 2,130 | 2,290 | 1,990 |
| 160° C. | 4,540 | 4,420 | 4,800 | 4,320 |
| 140° C. | 19,250 | 13,860 | 13,300 | 11,000 |
| 120° C. | 218,800 | 110,600 | 47,100 | 38,700 |

TABLE 4

Application data of sprayed compositions based on four different resins
(S-I-S Polymer: Kraton ® D-KX 602CS)

| Tackifying | Regalite ® | Regalite ® | RESIN I | Sample F |
|---|---|---|---|---|
| Resin | S 101 | S 260 | | |
| R & B spt. (° C.) | 102.6 | 102.3 | 102.8 | 101.8 |
| UV-alpha 268 nm | 0.66 | 2.16 | 2.87 | 3.5 |
| MMAP (° C.) | 76 | 66 | 54 | 47 |
| DACP (° C.) | 39 | 17 | 2 | −4 |
| Spiral Spray Bond Strength: Peel Adhesion (PE-Nonwoven, N/25 mm) | | | | |
| Peel Average | 4.1 | 4.8 | 5.8 | 5.1 |
| Peel Maximum | 6.0 | 7.4 | >9 | 7.8 |
| Comments | 15% FT/NW 85% AF/NW | 5% FT/NW 95% AF/PE | Total Substrate Failure | 10% FT/NW 45% AF/NW 45% AF/PE |

FT/NW = Fiber tear from nonwoven
AF/NW = Adhesion failure from nonwoven
AF/PE = Adhesion failure from polyethylene

| Tackifying | Regalite ® | Regalite ® | RESIN I | Sample F |
|---|---|---|---|---|
| R & B spt. (° C.) | 102.6 | 102.3 | 102.8 | 101.8 |
| UV-alpha 268 nm | 0.66 | 2.16 | 2.87 | 3.5 |
| MMAP (° C.) | 76 | 66 | 54 | 47 |
| DACP (° C.) | 39 | 17 | 2 | −4 |
| Spiral Spray Elastic Retention (in %) on Lycra ® (Creep resistance PE-Lycra ® -Nonwoven 300%) | | | | |
| (40° C., 1 hour) | 80 | 89 | 93 | 95 |
| (40° C., 2 hours) | 72 | 81 | 89 | 91 |
| (40° C., 3 hours) | 65 | 74 | 87 | 90 |
| (40° C., 4 hours) | 61 | 68 | 86 | 88 |
| Spiral Spray Elastic Retention (in %) on Latex (Creep resistance PE-Latex-Nonwoven 200%) | | | | |
| (40° C., 1 hour) | 71 | 76 | 81 | 85 |
| (40° C., 2 hours) | 66 | 73 | 80 | 82 |
| (40° C., 3 hours) | 62 | 73 | 79 | 80 |
| (40° C., 4 hours) | 60 | 72 | 79 | 80 |
| Spiral Spray Elastic Retention (in %) on Latex (Creep resistance PE-Latex-Nonwoven 300%) | | | | |
| (40° C., 1 hour) | 42 | 59 | 71 | 74 |
| (40° C., 2 hours) | 41 | 52 | 70 | 72 |
| (40° C., 3 hours) | 40 | 49 | 69 | 71 |
| (40° C., 4 hours) | 40 | 46 | 68 | 71 |

TABLE 5

Adhesive performance of five different resins
(S-I-S Polymer: Europrene ® Sol T 193B)

| Tackifying | Regalite ® | RESIN I | Piccolyte ® | Permalyn ® | ECR ® |
|---|---|---|---|---|---|
| Resin | S260 | | HM 106 | 6110 | 368LC |
| R & B spt. (° C.) | 101.7 | 102.8 | 107.1 | 101.8 | 102.1 |
| UV-alpha 268 nm | 2.29 | 2.87 | 1.83 | 1.69 | — |
| MMAP (° C.) | 61 | 54 | 53 | 3 | 62 |
| DACP (° C.) | 18 | 3 | 10 | −97 | 17 |
| Peel adhesion (N/25 mm) | | | | | |
| to Steel (23° C.) | 23.4 | 6.5 | 38.2 | 34.1 | 33.5 |
| to PE (23° C.) | 4.2 | 0.9 | 1.2 | 0.9 | 8.3 |
| Loop tack (N/25mm) | | | | | |
| to Steel (23° C.) | 31.2 | 8.6 | 30.1 | 35.2 | 53.1 |
| to PE (23° C.) | 6.1 | 0.2 | 1.0 | 1.5 | 1.8 |
| Needle Penetration | 85 | 69 | 81 | 97 | — |
| (23° C., dmm) | | | | | |
| Shear to steel (minutes) | | | | | |
| (23° C., 2.5 kg) | >10,000 | >10,000 | 4,723 | 5,274 | 4,051 |
| (40° C., 2.5 kg) | 377 | 225 | 184 | 92 | 90 |
| (70° C., 0.5 kg) | 57 | 45 | 69 | 23 | 91 |
| Shear to PE (minutes) | | | | | |
| (40° C., 1 kg) | 4,309 | 6,699 | 6,729 | 5,486 | — |
| SAFT (0.5 kg, ° C.) | 78 | 73 | 78 | 65 | 78 |
| Viscosity (mPa · s) at: | | | | | |
| 180° C. | 2,290 | 1,190 | 2,590 | 1,720 | 2,270 |
| 160° C. | 4,800 | 4,320 | 5,150 | 3,340 | 4,740 |
| 140° C. | 13,300 | 11,000 | 13,600 | 7,740 | 12,700 |
| 120° C. | 47,100 | 38,700 | 61,400 | 23,650 | 74,000 |

TABLE 6

Adhesive performance of two different resins in four different S-I-S copolymers

| Tackifying | Regalite ® | RESIN I | Regalite ® | RESIN I |
|---|---|---|---|---|
| Resin | S 260 | | S 260 | |
| R & B spt. (° C.) | 100.4 | 102.8 | 100.4 | 102.8 |
| UV-alpha 268 nm | 2.30 | 2.87 | 2.30 | 2.87 |
| MMAP (° C.) | 66 | 54 | 66 | 54 |
| DACP (° C.) | 17 | 2 | 17 | 2 |
| Polymer: | Europrene ® Sol TE 9407 | | Kraton ® D-KX 602CS | |
| | (35% styrene) | | (23% styrene) | |
| Loop tack (N/25 mm) | 24.2 | 4.8 | 21.1 | 17.8 |
| to Steel (23° C.) | | | | |
| Needle Penetration | — | 55 | 97 | 73 |
| (23° C., dmm) | | | | |
| Shear to steel (minutes) | 247 | 41 | 62 | 37 |
| (70° C., 0.5 kg) | | | | |
| SAFT (0.5 kg,° C.) | 85 | 77 | 78 | 74 |
| Viscosity 160 ° C. | 3,080 | 2,900 | 4,730 | 4,850 |
| (mPa · s) 140 ° C. | 9,900 | 8,900 | 12,980 | 13,000 |
| at: 120 ° C. | 62,000 | 39,300 | 49,400 | 46,500 |
| Polymer: | Vector ® 4211 | | Vector ® 4411 | |
| | (29% styrene) | | (44% styrene) | |
| Loop tack (N/25 mm) | 19.4 | 7.0 | 2.6 | 0.1 |
| to Steel (23° C.) | | | | |
| Needle Penetration | — | 63 | — | 27 |
| (23° C., dmm) | | | | |
| Shear to steel (minutes) | 143 | 19 | 620 | 88 |
| (70° C., 0.5 kg) | | | | |
| SAFT (0.5 kg, ° C.) | 82 | 75 | 87 | 81 |
| Viscosity 160 ° C. | 3,870 | 4,020 | 2,425 | 2,550 |
| (mPa · s) 140 ° C. | 11,100 | 10,600 | 7,960 | 7,840 |
| at: 120 ° C. | 52,600 | 42,900 | 54,000 | 39,600 |

TABLE 7

Rheological data of five different resins
(S-I-S Polymer: Kraton ® D-KX 602CS)

| Tackifying | Regalite ® | Regalite ® | Regalite ® | RESIN I | ECR ® |
|---|---|---|---|---|---|
| Resin | R101 | S101 | S260 | | 179A |
| R & B spt. (° C.) | 98.9 | 99.1 | 100.4 | 102.8 | 101.5 |
| UV-alpha 268 nm | 0.35 | 0.68 | 2.30 | 2.87 | 1.66 |
| MMAP (° C.) | 79 | 73 | 66 | 54 | 49 |
| DACP (° C.) | 42 | 38 | 17 | 2 | 33 |
| tan δ Peak | | | | | |
| Temperature (° C.) | 20.2 | 21.2 | 22.2 | 26.7 | 21.9 |
| Value | 4.78 | 4.68 | 3.79 | 2.56 | 3.91 |
| G' at 23° C. (kPa) | 99.2 | 107.0 | 156.0 | 450.0 | 126.0 |
| G' at 38° C. (kPa) | 34.1 | 34.2 | 41.5 | 62.0 | 37.0 |
| G' at 49° C. (kPa) | 26.4 | 26.4 | 31.2 | 40.0 | 28.1 |
| G' at 70° C. (kPa) | 23.0 | 22.6 | 23.9 | 24.5 | 20.9 |
| Cross-over Temperature (° C.) | 106.5 | 102.8 | 92.4 | 87.3 | 85.3 |

TABLE 8

Rheological data of five different resins
(S-I-S Polymer: Europrene ® Sol T 193B)

| Tackifying | Regalite ® | RESIN I | Piccolyte ® | Permalyn ® | ECR ® |
|---|---|---|---|---|---|
| Resin | S260 | | HM 106 | 6110 | 368LC |
| R & B spt. (° C.) | 101.7 | 102.8 | 107.1 | 101.8 | 102.1 |
| LV-alpha 268 nm | 2.29 | 2.87 | 1.83 | 1.69 | — |
| MMAP (° C.) | 61 | 54 | 53 | 3 | 62 |
| DACP (° C.) | 18 | 2 | 10 | -97 | 17 |
| tan δ Peak | | | | | |
| Temperature (° C.) | 22.9 | 28.4 | 25.5 | 26.5 | 20.9 |
| Value | 3.91 | 2.53 | 4.51 | 4.57 | 4.86 |
| G' at 23° C. (kPa) | 210.5 | 602.0 | 126.9 | 34.3 | 109.7 |
| G' at 38° C. (kPa) | 44.8 | 70.1 | 40.3 | 25.5 | 36.3 |
| G' at 49° C. (kPa) | 33.4 | 39.2 | 28.4 | 22.9 | 27.9 |
| G' at 70° C. (kPa) | 24.6 | 22.4 | 21.3 | 11.7 | 21.6 |
| Cross-over Temperature (° C.) | 93.0 | 88.2 | 97.6 | 79.1 | 97.1 |

TABLE 9

Adhesive performance of five different resins
(S-B-S Polymer: Stereon ® 840A)

| Tackifying Resin | Regalite ® S 101 | Regalite ® S 260 | RESIN I | Piccolyte ® HM 106 | Permalyn ® 6110 |
|---|---|---|---|---|---|
| R&B spt. (° C.) | 102.6 | 102.3 | 102.8 | 107.1 | 101.8 |
| UV-alpha 268 nm | 0.66 | 2.16 | 2.87 | 1.83 | 1.69 |
| MMAP (° C.) | 76 | 66 | 54 | 53 | 3 |
| DACP (° C.) | 39 | 17 | 2 | 10 | -97 |
| Peel adhesion (N/25 mm) | | | | | |
| to Steel (23° C.) | 20.8 | 21.2 | 15.6 | 27.6 | 20.5 |
| to PE (23° C.) | 3.2 | 9.6 | 8.7 | 10.1 | 9.1 |
| Loop tack (N/25 mm) | | | | | |
| to Steel (23° C.) | 17.3 | 35.1 | 30.6 | 35.1 | 29.9 |
| to PE (23° C.) | 4.8 | 16.9 | 15.3 | 11.2 | 8.2 |
| Needle Penetration (23° C., dmm) | 133 | 121 | 105 | 127 | 126 |

TABLE 9-continued

Adhesive performance of five different resins
(S-B-S Polymer: Stereon ® 840A)

| Tackifying Resin | Regalite ® S 101 | Regalite ® S 260 | RESIN I | Piccolyte ® HM 106 | Permalyn ® 6110 |
|---|---|---|---|---|---|
| Shear to steel (minutes) | | | | | |
| (23° C., 2.5 kg) | 413 | 533 | 670 | 700 | 524 |
| (40° C., 2.5 kg) | 28 | 43 | 64 | 90 | 46 |
| (70° C., 0.5 kg) | 19 | 37 | 37 | 50 | 30 |
| Shear to PE (minutes) | 238 | 224 | 593 | 1,736 | 575 |
| (40° C., 1 kg) | | | | | |
| SAFT (0.5 kg, ° C.) | 57 | 71 | 70 | 73 | 67 |
| Viscosity (mPa · s) at: | | | | | |
| 180° C. | 1,930 | 1,880 | 1,910 | 2,190 | 1,810 |
| 160° C. | 3,780 | 3,470 | 3,620 | 4,500 | 3,340 |
| 140° C. | 12,040 | 8,550 | 8,150 | 14,000 | 7,160 |
| 120° C. | 82,600 | 31,100 | 26,350 | 59,800 | 19,050 |

TABLE 10

Adhesive performance of four different resins
(S-V-S Polymer: Stereon ® 857)

| Tackifying Resin | Regalite ® R 101 | Regalite ® S 101 | Regalite ® S 260 | RESIN I |
|---|---|---|---|---|
| R&B spt. (° C.) | 101.5 | 102.6 | 102.3 | 102.8 |
| UV-alpha 268 nm | 0.30 | 0.66 | 2.16 | 2.87 |
| MMAP (° C.) | 81 | 76 | 66 | 54 |
| DACP (° C.) | 44 | 39 | 17 | 2 |
| Peel adhesion (N/25 mm) | | | | |
| to Steel (23° C.) | 23.1 | 27.3 | 17.2 | 7.9 |
| to PE (23° C.) | 1.1 | 2.3 | 1.7 | 0.8 |
| Loop tack (N/25 mm) | | | | |
| to Steel (23° C.) | 21.5 | 32.7 | 8.9 | 4.1 |
| to PE (23° C.) | 10.8 | 11.0 | 7.0 | 1.3 |
| Needle Penetration (23° C., dmm) | 106 | 113 | 101 | 80 |
| Shear to steel (minutes) | | | | |
| (23° C., 2.5 kg) | 1,664 | 2,870 | 4,515 | 3,428 |
| (40° C., 2.5 kg) | 90 | 163 | 277 | 318 |
| (70° C., 0.5 kg) | 34 | 48 | 72 | 56 |
| Shear to PE (minutes) | 3,471 | 3,320 | 1,891 | 8,387 |
| (40° C., 1 kg) | | | | |
| SAFF (0.5 kg, ° C.) | 76 | 78 | 83 | 79 |
| Viscosity (mPa · s) at: | | | | |
| 180° C. | 1,140 | 1,090 | 1,160 | 1,100 |
| 160° C. | 3,140 | 2,520 | 2,220 | 2,100 |
| 140° C. | 21,200 | 11,650 | 6,680 | 5,580 |
| 120° C. | 340,000 | 145,400 | 36,800 | 25,200 |

TABLE 11

Adhesive performance of four different resins
(S-B-S Polymer: Europrene ® Sol TE 6414)

| Tackifying Resin | Regalite ® S 260 | RESIN I | Piccolyte ® HM 106 | Permalyn ® 6110 |
|---|---|---|---|---|
| R&B spt. (° C.) | 102.3 | 102.8 | 107.1 | 101.8 |
| UV-alpha 268 nm | 2.16 | 2.87 | 1.83 | 1.69 |
| MMAP (° C.) | 66 | 54 | 53 | 3 |
| DACP (° C.) | 17 | 2 | 10 | −97 |
| Peel adhesion (N/25 mm) | | | | |
| to Steel (23° C.) | 13.6 | 13.0 | 21.5 | 18.7 |
| to PE (23° C.) | 9.0 | 7.5 | 4.0 | 7.9 |
| Loop tack (N/25 mm) | | | | |
| to Steel (23° C.) | 23.7 | 21.5 | 20.4 | 28.6 |
| to PE (23° C.) | 24.2 | 12.8 | 7.6 | 9.2 |
| Needle Penetration (23° C., dmm) | 80 | 74 | 86 | 89 |
| Shear to steel (minutes) | | | | |
| (23° C., 2.5 kg) | 794 | 7,247 | 4,264 | 10,153 |
| (40° C., 2.5 kg) | 64 | 291 | 344 | 170 |
| (70° C., 0.5 kg) | 47 | 39 | 72 | 23 |
| Shear to PE (minutes) | 749 | 911 | 2,968 | 716 |
| (40° C., 1 kg) | | | | |
| SAFT (0.5 kg, ° C.) | 78 | 77 | 80 | 75 |
| Viscosity (mPa · s) at: | | | | |
| 180° C. | 1,120 | 1,210 | 1,320 | 1,120 |
| 160° C. | 2,240 | 2,330 | 2,660 | 2,130 |
| 140° C. | 5,080 | 5,530 | 6,730 | 4,880 |
| 120° C. | 18,750 | 18,350 | 30,750 | 13,920 |

TABLE 12

Adhesive performance of two different resins in four different S-B-S copolymers

| Tackifying Resin | Regalite ® S 260 | RESIN I | Regalite ® S 260 | RESIN I |
|---|---|---|---|---|
| R&B spt. (° C.) | 100.4 | 102.8 | 100.4 | 102.8 |
| UV-alpha 268 nm | 2.30 | 2.87 | 2.30 | 2.87 |
| MMAP (° C.) | 66 | 54 | 66 | 54 |
| DACP (° C.) | 17 | 2 | 17 | 2 |
| Polymer: | Europrene ® Sol TE 6414 (40% styrene) | | Finaprene ® 602 (40% styrene) | |
| Loop tack (N/25 mm) to Steel (23° C.) | 26.5 | 23.0 | 33.7 | 23.6 |
| Shear to steel (minutes) | | | | |
| (23° C., 2.5 kg) | 412 | 3,464 | 516 | 3,111 |
| (40° C., 2.5 kg) | 48 | 174 | 45 | 504 |
| (70° C., 0.5 kg) | 50 | 12 | 15 | 27 |
| SAFT (0.5 kg, ° C.) | 75 | 74 | 74 | 69 |
| Viscosity (mPa · s) at: | | | | |
| 160° C. | 2,225 | 2,460 | 3,140 | 3,420 |
| 140° C. | 5,430 | 5,840 | 8,890 | 8,470 |
| 120° C. | 21,400 | 20,400 | 38,000 | 30,600 |
| Polymer: | Vector ® 4261 (29% styrene) | | Vector ® 4461 (43% styrene) | |
| Loop tack (N/25 mm) to Steel (23° C.) | 23.9 | 18.7 | 25.5 | 23.2 |
| Shear to steel (minutes) | | | | |
| (23° C., 2.5 kg) | 3,464 | >10,000 | 547 | >10,000 |
| (40° C., 2.5 kg) | 47 | 53 | 25 | 305 |
| (70° C., 0.5 kg) | 15 | 4 | 18 | 6 |
| SAFF (0.5 kg, ° C.) | 72 | 69 | 72 | 73 |
| Viscosity (mPa · s) at: | | | | |
| 160° C. | 5,740 | 6,210 | 2,620 | 2,870 |
| 140° C. | 12,880 | 14,200 | 6,680 | 6,850 |
| 120° C. | 38,400 | 40,600 | 24,850 | 24,500 |

TABLE 13

Rheological data of five different resins (S-B-S Polymer Stereon ® 840A)

| Tackifying Resin | Regalite ® S 101 | Regalite ® S 260 | RESIN I | Piccolyte ® HM 106 | Permalyn ® 6110 |
|---|---|---|---|---|---|
| R&B spt. (° C.) | 102.6 | 102.3 | 102.8 | 107.1 | 101.8 |
| UV-alpha 268 nm | 0.66 | 2.16 | 2.87 | 1.83 | 1.69 |
| MMAP (° C.) | 76 | 66 | 54 | 53 | 3 |
| DACP (° C.) | 39 | 17 | 2 | 10 | −97 |
| tan δ Peak | | | | | |
| Temperature (° C.) | 13.3 | 8.2 | 11.2 | 11.8 | 12.1 |
| Value | 3.31 | 4.13 | 2.87 | 4.10 | 4.11 |
| G' at 23° C. (kpa) | 52.2 | 41.8 | 65.0 | 48.3 | 45.0 |
| G' at 38° C. (kPa) | 22.2 | 27.9 | 35.6 | 25.8 | 26.6 |
| G' at 49° C. (kPa) | 17.9 | 23.4 | 27.4 | 21.2 | 20.9 |
| G' at 70° C. (kPa) | 13.6 | 15.4 | 15.2 | 14.9 | 10.5 |
| Cross-over Temperature (° C.) | 104.1 | 91.9 | 85.4 | 99.7 | 81.2 |

TABLE 14

Rheological data of five different resins (S-B-S Polymer: Europrene ® Sol T 168)

| Tackifying Resin | Regalite ® S 101 | Regalite ® S 260 | RESIN I | Piccolyte ® HM 106 | Permalyn ® 6110 |
|---|---|---|---|---|---|
| R&B spt. (° C.) | 102.6 | 102.3 | 102.8 | 107.1 | 101.8 |
| UV-alpha 268 nm | 0.66 | 2.16 | 2.87 | 1.83 | 1.69 |
| MMAP (° C.) | 76 | 66 | 54 | 53 | 3 |

TABLE 14-continued

Rheological data of five different resins
(S-B-S Polymer: Europrene ® Sol T 168)

| Tackifying Resin | Regalite ® S 101 | Regalite ® S 260 | RESIN I | Piccolyte ® HM 106 | Permalyn ® 6110 |
|---|---|---|---|---|---|
| DACP (° C.) | 39 | 17 | 2 | 10 | −97 |
| tan δ Peak | | | | | |
| Temperature (° C.) | 16.7 | 11.3 | 14.9 | 14.6 | 15.2 |
| Value | 3.51 | 3.87 | 2.31 | 4.14 | 3.67 |
| G' at 23° C. (kPa) | 75.0 | 58.3 | 125.0 | 65.6 | 74.0 |
| G' at 38° C. (kPa) | 27.5 | 35.3 | 48.5 | 30.9 | 37.0 |
| G' at 49° C. (kPa) | 22.4 | 30.4 | 35.6 | 26.3 | 29.0 |
| G' at 70° C. (kPa) | 19.9 | 23.7 | 22.1 | 22.2 | 16.7 |
| Cross-over Temperature (° C.) | 105.3 | 91.2 | 87.2 | 99.2 | 82.3 |

TABLE 15

Rheological data of five different resins
(S-B-S Polymer: Finaprene ® 417)

| Tackifying Resin | Regalite ® S 101 | Regalite ® S 260 | RESIN I | Piccolyte ® HM 106 | Permalyn ® 6110 |
|---|---|---|---|---|---|
| R&B spt. (° C.) | 102.6 | 102.3 | 102.8 | 107.1 | 101.8 |
| UV-alpha 268 nm | 0.66 | 2.16 | 2.87 | 1.83 | 1.69 |
| MMAP (° C.) | 76 | 66 | 54 | 53 | 3 |
| DACP (° C.) | 39 | 17 | 2 | 10 | −97 |
| tan δ Peak | | | | | |
| Temperature (° C.) | 9.5 | 5.8 | 6.9 | 8.5 | 9.1 |
| Value | 2.62 | 3.27 | 2.42 | 3.31 | 2.80 |
| G' at 23° C. (kPa) | 77.6 | 76.0 | 96.7 | 73.4 | 89.4 |
| G' at 38° C. (kPa) | 48.5 | 61.0 | 66.5 | 51.0 | 60.7 |
| G' at 49° C. (kPa) | 43.6 | 54.1 | 56.2 | 44.9 | 49.8 |
| G' at 70° C. (kPa) | 32.5 | 33.2 | 30.0 | 29.6 | 20.9 |
| Cross-over Temperature (° C.) | 95.6 | 85.6 | 80.7 | 90.5 | 74.7 |

TABLE 16

Rheological data of five different resins
(S-V-S Polymer: Stereon ® 857)

| Tackifying Resin | Regalite ® S 101 | Regalite ® S 260 | RESIN I | Piccolyte ® HM 106 | Permalyn ® 6110 |
|---|---|---|---|---|---|
| R&B spt. (° C.) | 102.6 | 102.3 | 102.8 | 107.1 | 101.8 |
| UV-alpha 268 nm | 0.66 | 2.16 | 2.87 | 1.83 | 1.69 |
| MMAP (° C.) | 76 | 66 | 54 | 53 | 3 |
| DACP (° C.) | 39 | 17 | 2 | 10 | −97 |
| tan δ Peak | | | | | |
| Temperature (° C.) | 17.3 | 17.1 | 21.4 | 19.9 | 21.5 |
| Value | 4.67 | 4.08 | 2.43 | 4.76 | 4.47 |
| G' at 23° C. (kPa) | 61.5 | 86.7 | 250.0 | 95.8 | 108.6 |
| G' at 38° C. (kPa) | 21.4 | 32.4 | 54.4 | 26.5 | 31.8 |
| G' at 49° C. (kPa) | 17.2 | 24.6 | 34.7 | 19.1 | 22.5 |
| G' at 70° C. (kPa) | 14.0 | 17.7 | 19.1 | 14.1 | 13.5 |
| Cross-over Temperature (° C.) | 112.6 | 99.2 | 92.4 | 105.2 | 89.7 |

Examples 17 Through 21

Masterbatch Evaluations

In tables 17 through 21 needle penetration and viscosity results are shown of S-B-S adhesives based on RESIN I in comparison with systems based on several commercially available tackifying resins, which are lower, equal, and higher in functionality. Five different resins are compared in adhesives based on five different S-B-S copolymers. The adhesive compositions from Examples 1 through 16 have all been mixed separately using a Z-blade mixer. During the high temperature blending process in a Z-blade mixer relatively high shear forces are developed which may cause a limited breakdown of the styrenic block copolymer. It should be understood, however, that the differences in adhesive performance because of polymer breakdown are usually very small. Nevertheless, to minimize possible small differences in adhesive performance caused by varying levels of polymer breakdown during the mixing process of adhesive compositions, the polymer and plasticizing oil ingredients may be separately blended together first. This polymer/oil blend is usually referred to as a masterbatch. To complete the adhesive composition the tackifying resin is blended in afterwards at significantly lower temperatures using low shear mixing equipment. In this way the final adhesive compositions made from a specific masterbatch will all have an equal level of polymer breakdown. In the case of the standard S-B-S adhesive formulation used to evaluate the adhesive compositions from Examples 17 through 21, the masterbatch comprises of 100 parts of S-B-S copolymer, 80 parts of Ondina® 7047 plasticizing oil, and 2 parts of Irganox® 1010 stabilizer. As indicated above the 220 parts of tackifying resin are incorporated afterwards in the composition, using low shear mixing equipment.

From the test results it can be concluded that although the systems based on Piccolyte® HM 106 Synthetic Resin and Permalyn® 6110 Rosin Ester respectively exhibit a similar or higher functionality compared with RESIN I, the compositions based on RESIN I explicitly demonstrate a superior adhesive performance, that is, both at low and high temperatures.

Due to its unique chemical structure RESIN I is more able to delay the order-disorder transition of the styrene end-blocks of the polymer than most of the other resins, with exception of the Permalyn® 6110 Rosin Ester compositions.

The compositions based on Regalite® S 101 Hydrogenated Hydrocarbon Resin and Piccolyte® HM 106 Synthetic Resin mostly exhibit a too high viscosity at 120° C. to ensure good wettability. The system based on Permalyno 6110 Rosin Ester exhibits low viscosities and superior wettability at high temperatures, but its cohesion performance below temperatures of about 45° C.–50° C. is lower compared with the adhesive based on RESIN I. This is clearly shown by the high needle penetration values for the compositions based on Permalyn® 6110 Rosin Ester, which indicate softer adhesives having a lower level of cohesive strength. In this respect, RESIN I shows the lowest needle penetration values in all five S-B-S copolymers. The superior cohesive strength of the RESIN I compositions is hereby illustrated perfectly. Also for compositions made according to the masterbatch method RESIN I offers the best balanced adhesive performance.

TABLE 17

Masterbatch performance of five different resins
(S-B-S Polymer: Europrene ® Sol T 168)

| Tackifying Resin | Regalite ® S 101 | Regalite ® S 260 | RESIN I | Piccolyte ® HM 106 | Permalyn ® 6110 |
|---|---|---|---|---|---|
| R&B spt. (° C.) | 102.6 | 102.3 | 102.8 | 107.1 | 101.8 |
| UV-alpha 268 nm | 0.66 | 2.16 | 2.87 | 1.83 | 1.69 |
| MMAP (° C.) | 76 | 66 | 54 | 53 | 3 |
| DACP (° C.) | 39 | 17 | 2 | 10 | −97 |
| Needle Penetration (23° C., dmm) | 95 | 98 | 87 | 108 | 99 |
| Viscosity (mPa · s) at: | | | | | |
| 180° C. | 2,930 | 2,780 | 2,910 | 3,260 | 3,500 |
| 160° C. | 5,810 | 5,360 | 5,620 | 6,480 | 6,380 |
| 140° C. | 17,620 | 13,600 | 12,850 | 19,200 | 14,350 |
| 120° C. | 121,400 | 51,200 | 43,100 | 93,000 | 39,000 |

TABLE 18

Masterbatch performance of five different resins
(S—B—S Polymer: Stereon ® 840 A)

| | Tackifying Resin | | | | |
|---|---|---|---|---|---|
| | Regalite ® S 101 | Regalite ® S 260 | RESIN I | Piccolyte ® HM 106 | Permalyn ® 6110 |
| R&B spt. (° C.) | 102.6 | 102.3 | 102.8 | 107.1 | 101.8 |
| UV-alpha 268 nm | 0.66 | 2.16 | 2.87 | 1.83 | 1.69 |
| MMAP (° C.) | 76 | 66 | 54 | 53 | 3 |
| DACP (° C.) | 39 | 17 | 2 | 10 | −97 |

TABLE 18-continued

Masterbatch performance of five different resins
(S—B—S Polymer: Stereon ® 840 A)

| | Tackifying Resin | | | | |
|---|---|---|---|---|---|
| | Regalite ® S 101 | Regalite ® S 260 | RESIN I | Piccolyte ® HM 106 | Permalyn ® 6110 |
| Needle Penetration (23° C., dmm) | 93 | 103 | 91 | 112 | 119 |
| Viscosity (mPa · s) at: | | | | | |
| 180° C. | 1,910 | 1,950 | 1,900 | 2,290 | 1,940 |
| 160° C. | 3,740 | 3,800 | 3,620 | 5,000 | 3,830 |
| 140° C. | 11,220 | 8,800 | 8,620 | 12,500 | 8,320 |
| 120° C. | 75,800 | 32,650 | 27,800 | 60,300 | 24,150 |

TABLE 19

Masterbatch performance of five different resins
(S—B—S Polymer: Finaprene ® 417)

| | Tackifying Resin | | | | |
|---|---|---|---|---|---|
| | Regalite ® S 101 | Regalite ® S 260 | RESIN I | Piccolyte ® HM 106 | Permalyn ® 6110 |
| R&B spt. (° C.) | 102.6 | 102.3 | 102.8 | 107.1 | 101.8 |
| UV-alpha 268 nm | 0.66 | 2.16 | 2.87 | 1.83 | 1.69 |
| MMAP (° C.) | 76 | 66 | 54 | 53 | 3 |
| DACP (° C.) | 39 | 17 | 2 | 10 | −97 |
| Needle Penetration (23° C., dmm) | 86 | 73 | 66 | 84 | 81 |
| Viscosity (mPa · s) at: | | | | | |
| 180° C. | 3,420 | 3,220 | 3,640 | 3,750 | 3,950 |
| 160° C. | 5,780 | 5,920 | 6,850 | 6,750 | 6,810 |
| 140° C. | 15,100 | 14,350 | 15,550 | 16,100 | 16,100 |
| 120° C. | 61,800 | 40,350 | 46,000 | 47,400 | 40,250 |

TABLE 20

Masterbatch performance of five different resins
(S—B—S Polymer: Vector ® 4261)

| | Tackifying Resin | | | | |
|---|---|---|---|---|---|
| | Regalite ® S 101 | Regalite ® S 260 | RESIN I | Piccolyte ® HM 106 | Permalyn ® 6110 |
| R&B spt. (° C.) | 102.6 | 102.3 | 102.8 | 107.1 | 101.8 |
| UV-alpha 268 nm | 0.66 | 2.16 | 2.87 | 1.83 | 1.69 |
| MMAP (° C.) | 76 | 66 | 54 | 53 | 3 |
| DACP (° C.) | 39 | 17 | 2 | 10 | −97 |
| Needle Penetration (23° C., dmm) | 97 | 85 | 79 | 89 | 97 |
| Viscosity (mPa · s) at: | | | | | |
| 180° C. | 2,860 | 3,380 | 3,340 | 3,400 | 3,330 |
| 160° C. | 5,320 | 5,880 | 6,100 | 6,370 | 6,180 |
| 140° C. | 12,350 | 15,250 | 13,020 | 14,000 | 13,000 |
| 120° C. | 46,200 | 38,700 | 37,350 | 44,000 | 33,250 |

TABLE 21

Masterbatch performance of five different resins
(S—B—S Polymer: Vector ® 4461)

|  | Tackifying Resin | | | | |
|---|---|---|---|---|---|
|  | Regalite ® S 101 | Regalite ® S 260 | RESIN I | Piccolyte ® HM 106 | Permalyn ® 6110 |
| R&B spt. (° C.) | 102.6 | 102.3 | 102.8 | 107.1 | 101.8 |
| UV-alpha 268 nm | 0.66 | 2.16 | 2.87 | 1.83 | 1.69 |
| MMAP (° C.) | 76 | 66 | 54 | 53 | 3 |
| DACP (° C.) | 39 | 17 | 2 | 10 | −97 |
| Needle Penetration (23° C., dmm) | 79 | 74 | 58 | 77 | 80 |
| Viscosity (mPa · s) at: | | | | | |
| 180° C. | 1,360 | 1,370 | 1,480 | 1,840 | 1,460 |
| 160° C. | 2,650 | 2,700 | 2,890 | 3,620 | 3,080 |
| 140° C. | 7,450 | 6,930 | 7,320 | 9,620 | 6,850 |
| 120° C. | 48,400 | 25,350 | 24,200 | 38,750 | 22,000 |

Adjusting the adhesive viscosity with aromatic resins:

In a further preferred embodiment of this invention the use of aromatic hydrocarbon resins is described to decrease the viscosity of hot-melt adhesives based on styrenic block copolymers, such as, but not limited to, S-I-S, S-B-S, S-V-S and (S-B)n block copolymers, including mixtures thereof and including modified and/or hydrogenated derivatives thereof. This is shown by reference to Examples 22 and 23.

In an attempt to decrease the adhesive viscosity of the various styrenic block copolymer based compositions, end-block compatible resins, such as, for example Kristalex® Synthetic Hydrocarbon Resin, were blended with same. It was found that such resins predominantly interact with the end-blocks of the styrenic copolymer, thereby delaying the order-disorder transition of the polymer end-blocks, which will result in lower adhesive viscosities.

The preferred end-block compatible tackifying resins under this separate embodiment include:

(a) aromatic petroleum hydrocarbons; and (b) polar or otherwise modified aromatic petroleum hydrocarbon resins such as, for example, copolymers and terpolymers of aromatic petroleum hydrocarbon resins with vinyl monomers, or mixtures thereof, such as vinyl arenes, vinyl pyridines, vinyl halides and vinyl carboxylates, including particularly those monovinyl aromatic hydrocarbons of the benzene series, such as, styrene, vinyl toluene, (alpha)-methyl-styrene, vinyl xylene, ethyl vinyl benzene, as well as dicyclic monovinyl compounds, such as, vinyl naphthalene and the like, as well as acrylic monomers, such as, acrylonitrile, methacrylonitrile, esters of acrylic acids, etc. Other modifying ingredients may be derived from alpha olefins, alkylene oxides, acetals, urethanes, natural rosins, phenols, etc.

Mixtures of two or more of the above described end-block compatible resins may be required for some formulations. Particularly preferred are copolymers and terpolymers of styrene, vinyl toluene and (alpha)-methyl-styrene.

To be most suitable for the purposes of the present invention, the end-block compatible resin of the present invention should preferably have:

(a) a Ring and Ball softening point of from about 50° C. to about 150° C., more preferably of from about 60° C. tc about 130° C., most preferably of from about 70° C. to about 120° C.;

(b) An MMAP cloudpoint of about 20° C. or less, more preferably 10° C. or less.

(c) A DACP cloudpoint of about 0° C. or less, more preferably −20° C. or less, most preferably −40° C. or less; and (d) An Mz value of about 15,000 Dalton or less, more preferably 10,000 Dalton or less, most preferably 5,000 Dalton or less.

More particularly, a preferred viscosity modifying aromatic resin of the present invention has the following properties:

(a) a R&B softening point of 60° C. to 130° C., (b) an MMAP cloudpoint of 10° C. or less, (c) a DACP cloudpoint of less than −20° C., and (d) an Mz value of 10,000 Dalton or less.

An even more preferred viscosity modifying aromatic resin or the present invention has the following properties:

(a) a R&B softening point of 70° C. to 120° C., (b) an MMAP cloudpoint of 10° C. or less, (c) a DACP cloudpoint of less than −40° C. and (d) an Mz value of 5,000 Dalton or less.

A particularly preferred example of an end-block compatible resin for the use in the hot-melt adhesive compositions of the present invention has the following typical properties:

| | |
|---|---|
| R&B softening point (° C.): | 100 |
| MMAP (° C.): | 2 |
| DACP (° C.): | −70 |
| Mn (Dalton): | 800 |
| Mw (Dalton): | 1,300 |
| Mz (Dalton): | 2,100 |

It should be understood that these end-block compatible resins were not designed as end-block reinforcing resins. End-block reinforcing resins, that is, high softening point and/or high molecular weight aromatic hydrocarbon resins, such as, for example Endex® 155 Hydrocarbon Resin or Kristalex® 3115 Hydrocarbon Resin usually do not delay the order-disorder transition of a styrenic block copolymer. The results of Examples 22 and 23 clearly indicate that hot melt adhesives, which were blended with such end-block reinforcing resins, have the noteworthy deficiency of an undesirable high viscosity, which will decrease the wettability and open-time of the system, making these systems unsuitable for spraying applications. When the systems are blended with lower molecular weight endblock compatible resins, a decrease in viscosity can be noticed. However, blending with low molecular weight endblock compatible resins such as Kristalex® Hydrocarbon Resins, that is, with especially those which have Ring and Ball softening points below about 115° C., also appears to soften the end-block domains of the styrenic block copolymer, which results in a significantly lower cohesive strength for the adhesive, either at ambient temperatures or at elevated temperatures. Since this is usually undesirable for the final performance of the hot-melt adhesive, the incorporation of such lower softening point end-block compatible resins was considered as disadvantageous and should therefore only be considered when the cohesive strength of the adhesive is already more than adequate.

It should be understood, however, that the hot-melt adhesive systems of the present invention exhibit superior adhesive performance because they have sufficient cohesion. This is explicitly demonstrated by the lower viscosities as well as the higher shear values at 23° C. and 40° C. for the systems based on RESIN I as the sole resin. The effect of such resins on the adhesive performance and the rheological behavior of an S-I-S based hot-melt construction adhesive is further illustrated by way of examples 22 through 25, which follow.

Examples 22 & 23

Tables 22 and 23 illustrate the effect of blending with various end-block compatible aromatic hydrocarbon resins on the adhesive performance of hot-melt adhesive systems based on Kraton® D-KX 602CS as the sole polymer and tackified with either Regalite® R 101 Hydrogenated Hydrocarbon Resin or RESIN I.

The results clearly indicate that the Kristalex® Hydrocarbon Resins, which have Ring and Ball softening points below about 115° C. and Mz values of maximum 3,000 are able to delay the order-disorder transition of the styrene end-blocks of the polymer.

This effect is explicitly illustrated by the lower SAFT values, lower shear values at 70° C., and the mostly lower viscosities at 120° C. of the systems blended with such lower softening point end-block compatible resins. The above mentioned differences appear to become even more apparent for systems based on Kristalex® Hydrocarbon Resins having decreasing softening points.

TABLE 22

Effect of blending with aromatic resins
(S—I—S Polymer: Kraton ® D-KX 602CS)
Base resin: 225 parts (90%)/Blending resin: 25 parts (10%)

| | Resin Blend: | | | | |
|---|---|---|---|---|---|
| | 100/0 | 90/10 | 90/10 | 90/10 | 90/10 |
| | | | Base resin: | | |
| | RESIN I | Regalite ® R 101 | RESIN I | Regalite ® R 101 | RESIN I |
| | | | Blending resin: | | |
| | Not Blended (250 parts) | Endex ® 155 | Endex ® 155 | Kristalex ® F 100 | Kristalex ® F 100 |
| R&B spt. (° C.) | — | 155.3 | 155.3 | 98.7 | 98.7 |
| MMAP (° C.) | — | 14 | 14 | 1 | 1 |
| DACP (° C.) | — | −7 | −7 | −73 | −73 |
| Mz (Dalton) | — | 12,000 | 12,000 | 2,250 | 2,250 |
| Peel adhesion (N/25 mm) | | | | | |
| to Steel (23° C.) | 17.3 | 35.8 | 5.0 | 34.7 | 8.5 |
| to PE (23° C.) | 4.1 | 8.2 | 0.3 | 9.2 | 1.0 |
| Loop tack (N/25 mm) | | | | | |
| to Steel (23° C.) | 17.8 | 46.4 | 1.3 | 49.5 | 13.9 |
| to PE (23° C.) | 1.4 | 22.7 | 0.3 | 19.1 | 1.6 |
| Needle Penetration (23° C., dmm) | 73 | 99 | 29 | 112 | 50 |
| Shear to steel (minutes) | | | | | |
| (23° C., 2.5 kg) | >88,000 | 25,537 | >88,000 | 4,744 | 78,421 |
| (40° C., 2.5 kg) | 651 | 231 | 72 | 173 | 338 |
| (45° C., 1.0 kg) | 33,201 | 33,777 | >50,000 | 14,679 | 12,894 |
| (50° C., 1.0 kg) | 975 | 7,792 | 4,707 | 1,601 | 568 |
| (60° C., 0.5 kg) | 206 | >20,000 | 1,935 | 15,017 | 135 |
| (70° C., 0.5 kg) | 37 | 669 | 54 | 159 | 22 |
| R&B spt. (° C.) | — | 155.3 | 155.3 | 98.7 | 98.7 |
| MMAP (° C.) | — | 14 | 14 | 1 | 1 |
| DACP (° C.) | — | −7 | −7 | −73 | −73 |
| Mz (Dalton) | — | 12,000 | 12,000 | 2,250 | 2,250 |
| Shear to PE (minutes) (40° C., 1 kg) | 44,644 | >70,000 | 59,958 | 5,283 | 53,126 |
| SAFT (0.5 kg, ° C.) | 77 | 90 | 79 | 84 | 72 |

TABLE 22-continued

Effect of blending with aromatic resins
(S—I—S Polymer: Kraton ® D-KX 602CS)
Base resin: 225 parts (90%)/Blending resin: 25 parts (10%)

| | Resin Blend: | | | | |
|---|---|---|---|---|---|
| | 100/0 | 90/10 | 90/10 | 90/10 | 90/10 |
| | | | Base resin: | | |
| | RESIN I | Regalite ® R 101 | RESIN I | Regalite ® R 101 | RESIN I |
| | | | Blending resin: | | |
| | Not Blended (250 parts) | Endex ® 155 | Endex ® 155 | Kristalex ® F 100 | Kristalex ® F 100 |
| Viscosity (mPa · s) at: | | | | | |
| 180° C. | 2,280 | 2460 | 2,900 | 1,860 | 2,550 |
| 160° C. | 4,850 | 5,620 | 6,020 | 3,840 | 4,840 |
| 140° C. | 13,000 | 21,100 | 20,000 | 11,800 | 13,250 |
| 120° C. | 46,500 | 208,800 | 70,600 | 73,700 | 48,200 |

TABLE 23

Effect of blending with aromatic resins
(S—I—S Polymer: Kraton ® D-KX 602CS)
Base resin: Regalite ® R101 - 225 parts (90%)/Blending resin - 25 parts (10%)

| | Resin Blend: | | | | |
|---|---|---|---|---|---|
| | 100/0 | 90/10 | 90/10 | 90/10 | 90/10 |
| | | | Blending resin: | | |
| | Not Blended (250 parts) | Kristalex ® 3115 | Kristalex ® F 100 | Kristalex ® F85 | Kristalex ® 3070 |
| R&B spt. (° C.) | — | 118.2 | 98.7 | 86.0 | 76.3 |
| MMAP (° C.) | — | 4 | 1 | 0 | 1 |
| DACP (° C.) | — | −49 | −73 | −88 | −112 |
| Mz (Dalton) | — | 3,265 | 2,250 | 1,660 | 1,171 |
| Peel adhesion (N/25 mm) | | | | | |
| to Steel (23° C.) | 32.8 | 31.7 | 347 | 31.6 | 32.5 |
| to PE (23° C.) | 7.8 | 8.5 | 9.2 | 9.0 | 12.7 |
| Loop tack (N/25 mm) | | | | | |
| to Steel (23° C.) | 43.2 | 52.0 | 49.5 | 48.0 | 47.8 |
| to PE (23° C.) | 12.1 | 19.1 | 19.1 | 14.0 | 16.4 |
| Needle Penetration (23° C., dmm) | 104 | 101 | 112 | 105 | 108 |
| Shear to steel (minutes) | | | | | |
| (23° C., 2.5 kg) | 2,406 | 8,383 | 4,744 | 3,358 | 2,688 |
| (40° C., 2.5 kg) | 137 | 144 | 173 | 109 | 91 |
| (45° C., 1.0 kg) | 2,459 | 28,988 | 14,679 | 39,171 | 4,943 |
| (50° C., 1.0 kg) | 1,466 | 3,802 | 1,601 | 2,645 | 2,454 |
| (60° C., 0.5 kg) | 7,953 | >20,000 | 15,017 | 3,409 | 2,514 |
| (70° C., 0.5 kg) | 290 | 390 | 159 | 62 | 92 |
| R&B spt. (° C.) | — | 118.2 | 98.7 | 86.0 | 76.3 |
| MMAP (° C.) | — | 4 | 1 | 0 | 1 |
| DACP (° C.) | — | −49 | −73 | −88 | −112 |
| Mz (Dalton) | — | 3,265 | 2,250 | 1,660 | 1,171 |
| Shear to PE (minutes) (40° C., 1 kg) | 4,304 | 10,671 | 5,283 | 5,185 | 2,330 |
| SAFT (0.5 kg, ° C.) | 88 | 86 | 84 | 80 | 81 |
| Viscosity (mPa · s) at: | | | | | |
| 180° C. | 2,020 | 2,400 | 1,860 | 1,920 | 1,940 |
| 160° C. | 4,350 | 4,820 | 3,840 | 3,840 | 3,790 |
| 140° C. | 13,900 | 15,000 | 11,800 | 12,450 | 11,200 |
| 120° C. | 126,000 | 136,000 | 73,700 | 73,600 | 67,800 |

Examples 24 & 25

Rheological evaluations

Tables 24 and 25 illustrate the effect of blending with various end-block compatible aromatic hydrocarbon resins on the Theological behavior of the S-I-S hot-melt adhesive systems from Tables 22 and 23, tackified with either Regalite® R 101 Hydrogenated Hydrocarbon Resin or RESIN I.

The results clearly indicate that the Kristalex® Hydrocarbon Resins, which have Ring and Ball softening points below about 115° C. are able to delay the order-disorder transition of the styrene end-blocks of the polymer.

However, adhesives based on blends of Regalite® R 101 Hydrogenated Hydrocarbon Resin with Kristalex® Hydrocarbon Resins, which have Ring and Ball softening points below about 115° C. did not result in an acceptable cross-over temperature according to the present invention. Also their G' values at temperatures below about 45° C.–50° C. are clearly lower compared with, in particular, the adhesive based on RESIN I. In addition to this, compositions based on RESIN I produce lower cross-over temperatures and lower tan δ peak values.

On the other hand, the RESIN I system in combination with both a Kristalex® F 100 hydrocarbon resin and an Endex ® 155 resin yielded a good tan δ peak value and a higher tan δ peak temperature, indicating a lower mid-block compatibility for this resin, that is, a reduced mobility of the continuous phase of the adhesive, which manifests itself in a higher cohesive strength for the system. Moreover, in comparison with the other systems, the results explicitly display a superior and best balanced adhesive performance for the hot-melt systems based on RESIN I as the sole resin.

TABLE 24

Rheological data of blended compositions from Table 22
Base resin: 225 parts (90%)/Blending resin: 25 parts (10%)

| | Base resin: | | | | |
|---|---|---|---|---|---|
| | RESIN I | Regalite ® R 101 | RESIN I | Regalite ® R 101 | RESIN I |
| | | | Blending resin: | | |
| | Not Blended (250 parts) | Endex ® 155 | Endex ® 155 | Kristalex ® F 100 | Kristalex ® F 100 |
| tan δ Peak | | | | | |
| Temperature (° C.) | 26.7 | 19.3 | 35.5 | 18.7 | 27.5 |
| Value | 2.56 | 4.27 | 1.10 | 4.90 | 1.87 |
| G' at 23° C. (kPa) | 450.0 | 94.0 | 3,000.0 | 78.0 | 810.0 |
| G' at 38° C. (kPa) | 62.0 | 37.5 | 420.0 | 32.1 | 91.0 |
| G' at 49° C. (kPa) | 40.0 | 30.9 | 140.0 | 26.3 | 48.2 |
| G' at 70° C. (kPa) | 24.5 | 27.1 | 47.0 | 23.0 | 24.9 |
| Cross-over Temperature (° C.) | 87.3 | 107.5 | 92.3 | 101.6 | 86.5 |

TABLE 25

Rheological data of blended compositions from Table 23
Base resin: Regalite ® R101 - 225 parts (90%)/Blending resin - 25 parts (10%)

| | Resin Blend: | | | | |
|---|---|---|---|---|---|
| | 100/0 | 90/10 | 90/10 | 90/10 | 90/10 |
| | | | Blending Resin: | | |
| | Not Blended (250 parts) | Kristalex ® 3115 | Kristalex ® F 100 | Kristalex ® F85 | Kristalex ® 3070 |
| tan δ Peak | | | | | |
| Temperature (° C.) | 20.2 | 19.3 | 18.7 | 18.1 | 17.4 |
| Value | 4.78 | 4.57 | 4.90 | 4.83 | 4.83 |
| G' at 23° C. (kPa) | 99.2 | 100.5 | 78.0 | 72.3 | 66.1 |
| G' at 38° C. (kPa) | 34.1 | 37.4 | 32.0 | 31.5 | 31.4 |
| G' at 49° C. (kPa) | 26.4 | 30.0 | 26.3 | 26.2 | 26.3 |
| G' at 70° C. (kPa) | 23.0 | 27.5 | 23.0 | 22.9 | 22.9 |
| Cross-over Temperature (° C.) | 106.5 | 104.7 | 101.6 | 101.0 | 99.5 |

MATERIALS & METHODS

Abbreviations

In the above examples and tables, the following abbreviations were used:

| | |
|---|---|
| R&B spt. | Ring and Ball softening point |
| UV-alpha 268 nm | UV-Absorption at 268 nm |
| MDSP (° C.) | Mettler Drop Softening Point |
| MMAP (° C.) | Mixed Methylcyclohexane Aniline Cloud Point |
| DACP (° C.) | Diacetone Alcohol Cloud Point |
| dmm | decimillimeters ($10^{-4}$ m) |
| SAFT | Shear Adhesion Failure Temperature |
| PE | Polyethylene |
| BOPP | Biaxially oriented Polypropylene Film |
| PSTC | Pressure Sensitive Tape Council |
| Mz | High molecular weight fraction of a resin (herein also named: z-average molecular weight). |
| FINAT | Federation Internationale des Fabricants et Transformateurs d'Adhesifs et Thermocollants sur papier et autres supports. |

Method for the preparation of the adhesives in the examples:

The adhesives were mixed for maximum 2 hours in a Werner & Pfleiderer LUK 2,5 K3, Z-blade mixer at temperatures of approximately 170° C., and coated with a Nordson Meltex CL170 laboratory coater onto released BOPP with coating weights of approximately 40 g/m². The coated tapes were slit into rolls of 5 cm width and stored overnight in a climatized room at 23° C. and 50% Relative Humidity. To determine the spiral spray bond strength the adhesives were not coated onto released BOPP, but sprayed, with coating weights of about 20 g/m², onto polyethylene film using a Nordson CF 1 controlled fiberization spiral spray head.

For the evaluation of the adhesive properties all coated BOPP samples were tested like a tape, predominantly according to PSTC tape test methods. For these tests the adhesive bonds were made in a climatized room at 23° C. and 50% Relative Humidity.

Following the formulation of the adhesive compositions which are summarized above, the following tests were performed:

Method for the determination of the R&B softening point:

The R&B softening point was determined according to ASTM D-36-70 with the Walter Herzog R&B apparatus, model MC-735.

Method for the determination of the MMAP cloudpoint of a resin:

The MMAP (Mixed Methylcyclohexane Cloud point) was determined using a modified ASTM D-611-82 procedure. The Methylcyclohexane is substituted for the Heptane used in the standard test procedure. The procedure uses Resin/Aniline/Methylcyclohexane in a ratio 1/2/1 (5 g/10 ml/5 ml), and the cloud point is determined by cooling a heated, clear blend of the three components until a complete turbidity just occurs.

Method for the determination of the DACP cloudpoint of a resin:

The DACP (Di-Acetone Alcohol Cloud Point) was determined using a modified ASTM D-611-82 procedure. For this method, the solvent mixture used in the standard test procedure is substituted by xylene and Di-Acetone Alcohol in a 1:1 volume blend. The procedure uses Resin/xylene/Di-Acetone Alcohol in a ratio 1/1/1 (5 g/5 ml/5 ml), and the cloud point is determined by cooling a heated, clear blend of the three components until a complete turbidity just occurs.

Method for the determination of the molecular weight of a resin:

The molecular weights Mn, Mw, Mz and the polydispersity (=Mw/Mn) were determined by size exclusion chromatography using polystyrene as comparative standard and a refractive index detector. For details, reference is made to the brochure "Selection Guide for Hercules Hydrocarbon Resins", published October 1993, No. 25.029E2, pages 14, 15 and 20.

Method for the determination of the resin color and color stability:

To determine the Gardner color the resin was mixed in a 1:1 blend (5 g/5 ml) with reagent grade toluene at room temperature until all the resin was dissolved. The color was determined spectrofotometically using the Dr. Lange LICO 200 apparatus. The color stability of the resin was measured according to the same method, that is, before the resin was dissolved in toluene, it was stored in an air circulated oven for 24 hours at a temperature of about 175° C.

Method for the determination of the UV-alpha 268 nm value of a resin:

The UV absorption of the resin at 268 nm (herein abbreviated UV alpha 268 nm) is determined using a Beckman DU-40 spectrophotometer. Approximately 50 mg resin sample is dissolved in reagent grade cyclohexane and diluted to the mark of a 50 ml flask. The UV absorption of the resin solution is measured at wavelengths of 268 nm and 400 nm respectively in a 1 cm quartz cuvet. As a reference sample, reagent grade cyclohexane is measured.

Calculation:

$$\text{UV-alpha 268 nm} = (\text{Ext 268 nm} - \text{Ext 400 nm})/(\text{Resin weight} \times 20)$$

Method for the determination of the Shear Adhesion Failure Temperature (SAFT) of an adhesive composition:

The Shear Adhesion Failure Temperature (SAFT) is determined in ° C. in the same manner as the PSTC-7 shear test, albeit that in this case the shear adhesion performance of the samples is not measured at a constant temperature and determined in minutes, but the temperature is measured at which shear adhesion failure takes place. To determine this SAFT temperature, the temperature of the oven, which starts at 30° C. is increased with a constant factor of 0.37° C. per minute.

The test is caried out in a mechanical convection oven. In this regard, two replicates of each of the samples were tested of which the average was reported.

Method for the determination of the Needle Penetration value of adhesive compositions:

This is a test of the hardness of each of the adhesive materials. In summary, a sample of each of the adhesive materials, formulated above, was exposed to a needle which has a 200 gram load applied thereto. This needle, and the associated 200 gram weight are placed on the surface of each of the adhesives and then permitted to freefall during the test for a period of approximately five seconds.

The depth of penetration of the needle is then measured and expressed in decimillimeters (dmm). The hardness test is performed in a climatized room at 23° C. and 50% relative humidity. This hardness determination is conducted in accordance with ASTM Method D-5 as modified for use with a 200 gram weight.

Method for the determination of PE-nonwoven Spiral Spray Bond Strength and Spiral Spray Elevated Temperature Resistance of adhesive compositions:

In these two tests, a spiral spray head was mounted on the Nordson hot-melt adhesive coater. The adhesives to be tested were applied through a 0.025" nozzle at an application temperature of approximately 160° C. Furthermore, in applying the adhesives, an air source was used which was heated internally in the nozzle to approximately 160° C. The adhesives to be tested were then sprayed onto a polyethylene substrate and combined with a nonwoven substrate after an open time of approximately 0.5 seconds. Following this procedure, the laminate was compressed between steel and rubber rollers with the laminate receiving a pressure of approximately 1.5 bar. The add-on level was approximately 20 grams per square meter. Following this procedure, the laminate constructions were then subjected to a 180° peel with an Instron Tensile tester at a cross-head speed of 5 cm per minute, as well as to a test utilizing a 100 gram weight and which is performed at 40° C., in a mechanical convection oven. In this regard, six replicates of each of the laminates were tested of which the average was reported.

Method for the determination of percent Elastic Retention or Creep Performance, of Elastic Attachments constructed with Spiral Sprayed Hot-Melt Adhesives:

A spiral spray head was again mounted on the Nordson hot-melt adhesive coater. The adhesives to be tested were applied through a 0.025" nozzle at an application temperature of approximately 160° C. Furthermore, in applying the adhesives, an air source was used which was heated internally in the nozzle to approximately 160° C. The adhesives to be tested were then sprayed onto a four-strand elastic which is backed up with a polyethylene substrate. After an open time of approximately 0.3 seconds the elastic was compressed between the polyethylene substrate and a nonwoven substrate. The laminate was compressed between compression rollers which included both steel and rubber, as described earlier. The laminate experienced a compression of 1.5 bar. The add-on level was 20 grams per square meter. The elastic was previously stretched to 300% (Lycra®) or 200% and 300% (latex). Following these steps, the creep resistance of the laminate was determined. In this test, a piece of about 25 cm length is cut of the laminate construction which beforehand is stretched to the original length of the polyethylene substrate. Following the cutting, the laminate construction is stretched to its original length again, after which it is attached to a sheet of corrugated material such as paper board or the like. Subsequently the nonwoven material and the elastic band are both cut under an angle of about 45°, without cutting the polyethylene substrate, in order to obtain a stretched and bonded laminate construction of about 20 cm length. The assembly is then placed in a mechanical convection oven at 40° C. Following this step, and at time intervals of 60, 120, 180 and 240 minutes, the bonded length is measured and the amount of delamination noted in % of the original length. In this regard, six replicates of each of the laminates were tested of which the average was reported. Separately, three replicates of each of the laminates are stored for a period of 24 hours in a climatized room at 23° C. and 50% Relative Humidity, after which the average amount of delamination is noted.

Method for the determination of the peel strength of an adhesive composition:

The peel strength is measured by the PSTC-1 test-method.

Method for the determination of the Loop tack of an adhesive composition:

The loop tack is measured by the FINAT-9 test-method.

Method for the determination of the shear strength of an adhesive composition:

The shear strengths were measured by the PSTC-7 test-method.

Method for the determination of the adhesive viscosity:

This characteristic was measured by employing conventional technology. In this regard, the viscosity of each of the adhesive formulations was measured at different temperatures, such as, for example, 120° C.; 140° C.; 160° C.; and 180° C., and is expressed herein in millipascal seconds (mPa.s).

A Brookfield Thermosel was employed to determine the viscosity. The viscosity measurement was done in accordance with ASTM Method D3236-73.

Method for the determination of the DMA properties of adhesive compositions:

The dynamic moduli G' and G" of the adhesive compositions were determined on a Rheometrics Mechanical Spectrometer (RDS-II) using 8 mm circular shaped parallel plates with a 2 mm gap distance over a temperature range from about −60° C. up to about 140° C. The frequency was kept fixed at 10 radians/sec. The strain was kept sufficiently high in order to get sufficient torque for the transducer.

Materials:

The Materials which were referred hereinabove by using trade names can more fully be described as follows Polymers:

Kraton® D-KX 602CS—A linear polystyrene-polyisoprene-polystyrene (S-I-S) triblock copolymer of Shell Chemical Company having a styrene content of about 23 wt %, and a di-block (S-I) content of about 20 wt %.

Europrene® Sol T 193B—A polystyrene-polyisoprene-polystyrene (S-I-S) triblock copolymer of Enichem Chemical Co having a styrene content of about 25 wt % and a melt flow rate of about 8 g/10 min.

Europrene® Sol TE 9407—A polystyrene-polyisoprene-polystyrene (S-I-S) triblock copolymer of Enichem Chemical Co. having a styrene content of about 35 wt % and a melt flow rate of about 8 g/10 min.

Vector® 4211—A linear polystyrene-polyisoprene-polystyrene (S-I-S) triblock copolymer supplied by Dexco Polymers having a styrene content of 29 wt %, melt flow rate of 12 g/10 min and 0 wt % diblock (S-I).

Vector® 4411—A linear polystyrene-polyisoprene-polystyrene (S-I-S) triblock copolymer supplied by Dexco Polymers having a styrene content of 44 wt %, melt flow rate of 40 g/10min and 0 wt % diblock (S-I).

Stereon® 840A—A polystyrene-polybutadiene-polystyrene (S-B)n multi-block copolymer of Firestone Synthetic Rubber & latex Company, having a styrene content of about 44.5 wt % and a melt flow rate of 11.5 g/10 min.

Stereon® 857—A polystyrene-polyvinylbutadiene-polystyrene (S-V-S) block copolymer of Firestone Synthetic Rubber & latex Company, having a styrene content of about 44 wt %, a vinyl content of about 57% and a melt flow rate of 13 g/10 min.

Europrene® Sol T 168—A polystyrene-polybutadiene-polystyrene (S-B-S) block copolymer of Enichem Chemical Co having a styrene content of about 44 wt % and a melt flow rate of about 9 g/10 min.

Europrene® Sol TE 6414—A polystyrene-polybutadiene-polystyrene (S-B-S) block copolymer of Enichem Chemical Co having a styrene content of about 40 wt % and a melt flow rate of about 12 g/10 min.

Finaprene® 602—A polystyrene-polybutadiene-polystyrene (S-B-S) radial block copolymer of Fina Oil & Chemical Company having a styrene content of about 40 wt % and a melt flow rate of about 8 g/10 min.

Finaprene® 417—A polystyrene-polybutadiene-polystyrene (S-B-S) radial block copolymer of Fina Oil & Chemical Company having a styrene content of about 29 wt %.

Vector® 4261—A polystyrene-polybutadiene-polystyrene (S-B-S) block copolymer supplied by Dexco Polymers having a styrene content of 29 wt %, melt flow rate of 40 g/10 min and 0 wt % diblock (S-B).

Vector® 4461—A polystyrene-polybutadiene-polystyrene (S-B-S) triblock copolymer supplied by Dexco Polymers having a styrene content of 43 wt %, melt flow rate of 23 g/10 min and 0 wt % diblock (S-B).

Tackifying Resins:

Regalite® R 101 Hydrogenated Hydrocarbon Resin—A fully hydrogenated C9-aromatic petroleum resin available from Hercules B.V. having a Ring & Ball softening point of about 100° C., an MMAP cloudpoint of about 75° C., a DACP cloudpoint of about 45° C., and an Mz value of about 1,200 Dalton.

Regalite® S 101 Hydrogenated Hydrocarbon Resin—A partially hydrogenated C9-aromatic petroleum resin available from Hercules B.V. having a Ring & Ball softening point of about 100° C., an MMAP cloudpoint of about 70° C., a DACP cloudpoint of about 35° C., and an Mz value of about 1,300 Dalton.

Regalite® S 260 Hydrogenated Hydrocarbon Resin—A partially hydrogenated C9-aromatic petroleum resin available from Hercules B.V. having a Ring & Ball softening point of about 100° C., an MMAP cloudpoint of about 60° C., a DACP cloudpoint of about 17° C., and an Mz value of about 1,500 Dalton.

Permalyn® 6110 Rosin Ester—A stabilized pentaerythritol ester of gum rosin available from Hercules B.V. having a Ring & Ball softening point of about 100° C., an MMAP cloudpoint of about 3° C., a DACP cloudpoint of about −97° C., and an Mz value of about 1,200 Dalton.

Piccolyte® HM 106 Hydrocarbon Resin—A styrenated polyterpene resin available from Hercules B.V. having a Ring & Ball softening point of about 105° C., an MMAP cloudpoint of about 53° C., a DACP cloudpoint of about 10° C., a UV alpha of 1.8 to 1.9 and an Mz value of about 1,500 Dalton.

ECR® 368LC—A hydrogenated resin available from Exxon Chemical Company having a Ring & Ball softening point of about 100° C., an MMAP cloudpoint of about 62° C., a DACP cloudpoint of about 17° C., and an Mz value of about 2,000 Dalton.

ECR® 179A—A hydrogenated resin available from Exxon Chemical Company having a Ring & Ball softening point of about 100° C., an MMAP cloudpoint of about 50° C., a DACP cloudpoint of about 35° C., and an Mz value of about 1,600 Dalton.

Other modifying resins:

Endex® 155 Synthetic Hydrocarbon Resin—A pure monomer aromatic petroleum resin available from Hercules Incorporated having a Ring & Ball softening point of about 155° C., an MMAP cloudpoint of about 14° C., a DACP cloudpoint of about −7° C., and an Mz value of about 12,000 Dalton.

Kristalex® 3115 Synthetic Hydrocarbon Resin—A pure monomer aromatic petroleum resin available from Hercules Incorporated having a Ring & Ball softening point of about 120° C., an MMAP cloudpoint of about 4° C., a DACP cloudpoint of about −50° C., and an Mz value of about 3,200 Dalton.

Kristalex® F 100 Synthetic Hydrocarbon Resin—A pure monomer aromatic petroleum resin available from Hercules B.V. having a Ring & Ball softening point of about 100° C., an MMAP cloudpoint of about 2° C., a DACP cloudpoint of about −75° C., and an Mz value of about 2,200 Dalton.

Kristalex® F 85 Synthetic Hydrocarbon Resin—A pure monomer aromatic petroleum resin available from Hercules B.V. having a Ring & Ball softening point of about 85° C., an MMAP cloudpoint of about 1° C., a DACP cloudpoint of about −90° C., and an Mz value of about 1,800 Dalton.

Kristalex® 3070 Synthetic Hydrocarbon Resin—A pure monomer aromatic petroleum resin available from Hercules Incorporated having a Ring & Ball softening point of about 70° C., an MMAP cloudpoint of about 1° C., a DACP cloudpoint of about −110° C., and an Mz value of about 1,200 Dalton. Other ingredients:

Ondina® 7047—A paraffinic/naphthenic (70/30) extender oil available from Shell Chemical Company.

Irganox® 1010—An antioxidant mainly pentaerythrityl-tetrakis[3-(3,5-di-tert.butyl-4-hydroxyphenyl)-propionate] as commercial sample from Ciba-Geigy Chemical Company.

What we claim is:

1. A hot-melt adhesive composition which comprises:
   (a) about 50 to about 150 parts by weight of a styrenic block copolymer;
   (b) about 20 to about 450 parts by weight of a tackifying resin which, when incorporated into a reference composition consisting of 100 parts by weight of a styrene-isoprene-styrene copolymer having a styrene content of about 20 to 30% by weight, 250 parts by weight of said tackifying resin, 50 parts by weight of a paraffinic/napthenic (70/30 weight/weight) extender oil and 2 parts by weight of a stabilizer consisting essentially of pentaerythrityl-tetrakis[3-(3,5-di-tert.butyl-4-hydroxyphenyl)-propionate], leads to the following properties of said reference composition:
      a melt viscosity of about 60,000 mPa.s or less at a temperature of about 120° C.;
      a tan δ value of about 3.5 or less, wherein tan δ is defined as the ratio between the loss modulus (G") and the storage modulus (G') of said composition;
      an elastic retention on natural latex rubber (200%) after 4 h at about 40° C. of about 70% or more; and
      a crossover temperature between G' and G" (tan δ=1) of about 95° C. or less,
   wherein G" and G' of said composition are determined on a Rheometrics Mechanical Spectrometer (RDS-II) using 8 mm circular shaped parallel plates with a 2 mm gap distance over a temperature range from about −60° C. up to about 140° C. and a frequency of 10 radians/sec.

2. The hot-melt adhesive composition of claim 1 wherein the tackifying resin (b) has a Ring and Ball (R&B) softening point of about 50° C. to about 150° C., and is a resin or resin mixture selected from the group consisting of natural, dimerized and polymerized rosins.

3. The hot-melt adhesive composition of claim 2 wherein the tackifying resin is hydrogenated or hydrotreated.

4. The hot-melt adhesive composition of claim 1 wherein the tackifying resin (b) has a Ring & Bell softenting point of about 50° C. to about 150° C., and is a resin or resin mixture selected from the group consisting of polyterpene resins.

5. The hot-melt adhesive composition of claim 4 wherein the tackifying resin is hydrogenated or hydrotreated.

6. The hot-melt adhesive composition of claim 1 wherein the tackifying resin (b) has a Ring & Bell softenting point of about 50° C. to about 150° C., and is a resin or resin mixture selected from the group consisting of copolymers and terpolymers of natural terpenes.

7. The hot-melt adhesive composition of claim 6 wherein the tackifying resin is hydrogenated or hydrotreated.

8. The hot-melt adhesive composition of claim 1 wherein the tackifying resin (b) has a Ring and Ball softening point of about 50° C. to about 150° C., and is a resin or resin mixture selected from the group consisting of polar terpene resins.

9. The hot-melt adhesive composition of claim 8 wherein the tackifying resin is hydrogenated or hydrotreated.

10. The hot-melt adhesive composition of claim 1 wherein the tackifying resin (b) has a Ring & Bell softening point of about 50° C. to about 150° C., and is a resin or resin mixture comprising aliphatic petroleum hydrocarbon resins.

11. The hot-melt adhesive composition of claim 10 wherein the tackifying resin is hydrogenated or hydrotreated.

12. The hot-melt adhesive composition of claim 1 wherein the tackifying resin (b) has a Ring & Bell softening point of about 50° C. to about 150° C., and is a resin or resin mixture comprising aromatic petroleum hydrocarbon resins.

13. The hot-melt adhesive composition of claim 12 wherein the tackifying resin is hydrogenated or hydrotreated.

14. The hot-melt adhesive composition of claim 1 wherein the tackifying resin (b) has a Ring & Bell softening point of about 50° C. to about 150° C., and is a resin or resin mixture comprising aliphatic/aromatic petroleum derived hydrocarbon resins.

15. The hot-melt adhesive composition of claim 14 wherein the tackifying resin is hydrogenated or hydrotreated.

16. The hot-melt adhesive composition of claim 1 wherein the tackifying resin (b) has a Ring and Ball softening point of about 50° C. to about 150° C., and is a resin or resin mixture comprising polar aliphatic and/or aromatic petroleum hydrocarbon resins.

17. The hot-melt adhesive composition of claim 16 wherein the tackifying resin is hydrogenated or hydrotreated.

18. The hot-melt adhesive composition of claim 1 wherein the tackifying resin (b) is a partially hydrogenated aromatic hydrocarbon resin having the following properties:
   (i) a Ring & Bell softening point of about 50° C. to about 150° C.;
   (ii) a mixed methylcyclohexane aniline cloudpoint (MMAP) of about 10° C. to about 75° C.;
   (iii) a Di-Acetone Alcohol cloudpoint (DACP) of about 35° C. or less;
   (iv) a z-average molecular weight (Mz) of about 10,000 Dalton or less; and
   (v) a UV absorbance at 268 nm (UV alpha) ranging from about 2.0 to about 5.0.

19. The hot-melt adhesive composition of claim 18 wherein the tackifying resin (b) is a partially hydrogenated aromatic C9 hydrocarbon resin having the following properties:

| | |
|---|---|
| Ring and Ball softening point (° C.) | 100 ± 5° C. |
| MMAP (° C.) | 52 ± 5° C. |
| DACP (° C.) | 2 ± 5° C. |
| UV-alpha 268 nm | 2.9 ± 0.2 |
| Mz (Dalton) | 1,500 ± 30. |

20. The hot-melt adhesive composition of claim 1 characterized in that the styrenic block copolymer (a) is selected from
   (a') copolymers wherein the respective monomeric moieties are arranged in an alternating sequence having the general sequence of A-B-A or A-B-A-B-A.-B-; and/or
   (a") teleblock copolymers wherein at least three branches radially extend outwardly from a central hub, and wherein each of the branches have terminal blocks "A" and an elastomeric segment "B" in the center;
   wherein "A" represents a non-elastomeric block selected from the group consisting of polystyrene, homopolymers or copolymers of vinyl monomers, alpha olefins, alkylene oxides, acetals and urethanes and "B" represents an unvulcanized elastomeric block selected from the group consisting of isoprene, butadiene, vinyl isoprene or vinyl butadiene, and hydrogenated versions thereof.

21. The hot-melt adhesive composition of claim 20 wherein the tackifying resin (b) is a partially hydrogenated aromatic hydrocarbon resin having the following properties:
   (i) a Ring & Bell softening point of about 50° C. to about 150° C.;
   (ii) a mixed methylcyclohexane aniline cloudpoint (MMAP) of about 10° C. to about 75° C.;
   (iii) a Di-Acetone Alcohol cloudpoint (DACP) of about 35° C. or less;
   (iv) a z-average molecular weight (Mz) of about 10,000 Dalton or less; and
   (v) a UV absorbance at 268 nm (UV alpha) ranging from about 2.0 to about 5.0.

22. The hot-melt adhesive composition of claim 1 which further includes >0 to about 150 parts by weight of (c) a plasticizing oil.

23. The hot-melt adhesive composition of claim 22 wherein the plasticizing oil (c) is selected from the group consisting of naphthenic/paraffinic oils, olefinic oligomers, low molecular weight polymers, vegetable and animal oils including glycerol esters of fatty acids and polymerization products thereof, liquid resins and hydrogenated versions of these compounds.

24. The hot-melt adhesive composition of claim 1 which further includes >0 to about 4 parts by weight of (d) a stabilizer.

25. The hot-melt adhesive composition of claim 1 which further includes 100 or less parts by weight of (e) a viscosity modifying aromatic resin having the following properties:
   an Ring & Bell softening point of 50° C. to 150° C.;
   an MMAP cloudpoint of 20° C. or less
   a DACP cloudpoint of 0° C. or less, and
   an Mz value of 15,000 Dalton or less.

26. The hot-melt adhesive composition according to claim 25 wherein the viscosity modifying aromatic resin (e) is selected from the group consisting of:
   (e') aromatic petroleum hydrocarbons; and
   (e") polar aromatic petroleum hydrocarbon resins, including copolymers and terpolymers of aromatic petroleum hydrocarbon resins with vinyl monomers and/or acrylic monomers, and mixtures thereof.

27. The hot-melt adhesive composition according to claim 26 wherein the viscosity modifying aromatic resin (e) is selected from the group consisting of copolymers and terpolymers of styrene, vinyl toluene and (alpha)-methylstyrene.

28. A partially hydrogenated hydrocarbon resin having the following properties:
   (a) a Ring & Bell softening point of about 50° C. to about 150° C.;
   (b) a mixed methylcyclohexane aniline cloudpoint (MMAP) of about 10° C. to about 75° C.;
   (c) a Di-Acetone Alcohol cloudpoint (DACP) of about 35° C. or less;
   (d) a z-average molecular weight (Mz) of about 10,000 Dalton or less; and (e) a UV absorbance at 268 nm ranging from about 2.0 to about 5.0.

29. The resin according to claim 28 wherein the Ring & Bell value ranges from about 60° C. to about 140° C., the MMAP ranges from about 20° C. to about 70° C., the DACP is about 25° C. or less; the Mz is about 5,000 Dalton or less, and the UV absorbance at 268 nm is about 2.7 to about 3.1.

30. The resin of claim 28 wherein the R&B value ranges from 75° C. to 135° C.; the DACP is 15° C. or less and the Mz is 3,000 Dalton or less.

31. The resin according to claim 28 which is a partially hydrogenated aromatic C9 hydrocarbon resin having the following properties:

| | |
|---|---|
| Ring and Ball softening point (° C.) | 100 ± 5° C. |
| MMAP (° C.) | 52 ± 5° C. |
| DACP (° C.) | 2 ± 5° C. |
| UV-alpha 268 nm | 2.9 ± 0.2 |
| Mz (Dalton) | 1,500 ± 30%. |

32. A process for preparing a partially hydrogenated hydrocarbon resin comprising the following steps:

(a) providing an unsaturated aromatic feedstream predominantly containing monomers having about 7 to about 10 carbon atoms;

(b) polymerizing the unsaturated aromatic feedstream through Friedel-Crafts polymerization to form a polymerized feedstream; and (c) partially hydrogenating the polymerized feedstream to produce a partially hydrogenated hydrocarbon resin wherein the partially hydrogenated hydrocarbon resin has the following properties:

(i) a Ring and Ball softening point of about 50° C. to about 150° C.;

(ii) a mixed methylcyclohexane aniline cloudpoint (MMAP) of about 10° C. to about 75° C.;

(iii) a Di-Acetone Alcohol cloudpoint (DACP) of about 35° C. or less;

(iv) a z-average molecular weight (Mz) of about 10,000 Dalton or less; and (v) a UV absorbance at 268 nm ranging from about 2.0 to about 5.0.

33. The process for preparing a partially hydrogenated hydrocarbon resin of claim 32 further comprising the step of:

(d) stripping the partially hydrogenated polymerized feedstream to adjust the Ring & Bell softening point of the partially hydrogenated hydrocarbon resin.

* * * * *